United States Patent
Shyam

(10) Patent No.: US 11,847,379 B1
(45) Date of Patent: Dec. 19, 2023

(54) AUDIO PROCESSING METHOD AND SYSTEM FOR ENVIRONMENTAL ENRICHMENT THERAPY

(71) Applicant: Blackbird Neuroscience Inc., Arlington, MA (US)

(72) Inventor: Rishab R. Shyam, Arlington, MA (US)

(73) Assignee: Blackbird Neuroscience Inc., Arlington, MA (US)

( * ) Notice: Subject to any disclaimer, the term of this patent is extended or adjusted under 35 U.S.C. 154(b) by 0 days.

(21) Appl. No.: 17/952,146

(22) Filed: Sep. 23, 2022

(51) Int. Cl.
*G06F 3/16* (2006.01)
*H04R 3/00* (2006.01)
*A61B 5/00* (2006.01)

(52) U.S. Cl.
CPC .............. *G06F 3/165* (2013.01); *G06F 3/162* (2013.01); *H04R 3/00* (2013.01); *A61B 5/4082* (2013.01)

(58) Field of Classification Search
CPC ........... G06F 16/635; A63B 2071/0625; A63B 71/0686
USPC ............................ 381/101, 102, 103; 700/94
See application file for complete search history.

(56) References Cited

U.S. PATENT DOCUMENTS

| | | | |
|---|---|---|---|
| 9,526,946 B1 * | 12/2016 | Zets | G09B 19/0038 |
| 9,974,478 B1 | 5/2018 | Brokaw et al. | |
| 10,437,335 B2 | 10/2019 | Daniels | |
| 2011/0184225 A1 | 7/2011 | Whitall et al. | |
| 2017/0290290 A1 * | 10/2017 | Trottier | A01K 5/0291 |
| 2017/0296116 A1 | 10/2017 | McCarthy et al. | |
| 2019/0022351 A1 | 1/2019 | McCarthy et al. | |
| 2020/0121544 A1 * | 4/2020 | George | A61H 9/00 |
| 2022/0345834 A1 * | 10/2022 | Fischer | H04R 25/505 |

OTHER PUBLICATIONS

Young, William R. et al., Auditory cueing in Parkinson's patients with freezing of gait. What matters most: Action-relevance or cue-continuity? Neuropsychologia 87: 54-62 (2016). Elsevier Ltd.

* cited by examiner

*Primary Examiner* — Alexander Krzystan
(74) *Attorney, Agent, or Firm* — Gregory Finch; Finch Paolino, LLC

(57) ABSTRACT

An audio processing method and system configured to output at least one clinically-validated cue or combination of cues targeting at least one symptom or aspect of a CNS disease, disorder or condition to at least one user. In accordance with certain embodiments, the at least one clinically-validated cue or combination of cues comprises an audio cue. An audio processing method of the present disclosure comprises one or more steps or operations for selecting at least one audio file comprising a clinically-validated audio cue from a plurality of audio files comprising a plurality of clinically-validated audio cues, applying one or more audio rendering parameters to the at least one audio file, and outputting an acoustic output of one or more audio files to a user for a specified duration.

20 Claims, 16 Drawing Sheets

AUDIO PROCESSING METHOD AND SYSTEM FOR ENVIRONMENTAL ENRICHMENT THERAPY

FIELD

The present disclosure relates to the field of audio processing methods and systems in digital therapeutics; in particular, an audio processing method and system for treatment of CNS disorders, diseases and conditions.

BACKGROUND

Central nervous system (CNS) disease is a broad category of conditions in which the brain does not function as it should, limiting health and the ability to function. The condition may be an inherited metabolic disorder; the result of damage from an infection, a degenerative condition, stroke, a brain tumor or other problem; or arise from unknown or multiple factors. Movement disorders such as Parkinson's Disease, Parkinsonism, Secondary Parkinsonism, Amyotrophic Lateral Sclerosis, Fragile X Tremor Associated Syndrome, traumatic brain injury, spinal cord injury, indications requiring physical therapy/rehab, Huntington's Disease, spinal muscular atrophy, stroke rehabilitation, Duchenne Muscular Dystrophy, gait disorders, walking disorders, ataxia, cervical dystonia, chorea, dystonia, functional movement disorder, multiple system atrophy, myoclonus, progressive supranuclear palsy, restless legs syndrome, tardive dyskinesia, Tourette syndrome, tremor, Wilson's Disease, Rett syndrome, Spasticity, Lewy body dementia, Blepharospasm and hemifacial spasm are all examples of CNS diseases, disorders and/or conditions. What each of these diseases, disorders and/or conditions have in common is the loss of sufficient, intact nervous system circuits that orchestrate functions as varied as memory formation (in Alzheimer's) or voluntary motion (in movement disorders).

There are a variety of treatment approaches and technologies directed to CNS diseases, disorders and/or conditions. Many prior art solutions as well as burgeoning therapeutic approaches that target CNS conditions are focused on gene therapy or RNA modification to correct specific defects that might be potentially driving the underlying disease or disorder. These approaches, largely driven by adeno-associated viruses for delivery of effector payloads, or via intrathecal injection of RNA based therapies, continue to be limited in their translation in the clinic due to toxicity, specificity, and use case scenario challenges. Small molecule therapies, which continue to remain as the mainstay for treatment, are blunt instruments that either turn OFF or ON the CNS receptor/neurotransmitter function.

Certain prior art solutions have attempted to treat certain CNS disorders, such as Parkinson's disease, through the use of external stimuli and sensory cueing. The notion of sensory cueing in Parkinson's relates to the provision of either spatial cues that inform where movements should be guided (e.g., horizontal lines placed on the floor), or temporal cues that inform when a movement should be executed (e.g., an auditory metronome). Such improvements are often demonstrated in the context of reducing gait variability when patients walk on static visual targets and/or attempt to step in time to a metronome. Severe gait deficits such as freezing of gait often persist despite optimal pharmacological or surgical intervention.

Through applied effort, ingenuity, and innovation, Applicant has identified a number of deficiencies and problems with sensory cueing methods and systems in the context of treatment of CNS disorders, diseases and conditions. Applicant has developed a solution that is embodied by the present invention, which is described in detail below.

SUMMARY

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

Certain aspects of the present disclosure provide for an audio-processing method for environmental enrichment therapy comprising selecting, with a processor, a first audio file from a plurality of audio files according to a therapeutic protocol, wherein the first audio file comprises an audio cue comprising a recorded or artificial sound from an environment; applying, with the processor, one or more audio rendering parameters to the first audio file according to the therapeutic protocol to generate a rendered audio file, wherein the audio rendering parameters comprise parameters for manipulating one or more audio features of the first audio file, wherein the one or more audio features comprise one or more acoustic properties; and outputting, with the processor operably engaged with a loudspeaker, an acoustic output of the rendered audio file to a listener for a specified duration, wherein the therapeutic protocol comprises parameters for selecting the first audio file from the plurality of audio files and configuring the one or more audio rendering parameters.

In accordance with certain aspects of the present disclosure, the audio-processing method may further comprise one or more steps or operations for selecting, with the processor, a second audio file from the plurality of audio files, wherein the second audio file comprises a recording of a different audio cue from the first audio file. In accordance with certain aspects of the present disclosure, the audio-processing method may further comprise one or more steps or operations for outputting, with the processor operably engaged with the loudspeaker, an acoustic output of the second audio file sequentially or concomitantly with the acoustic output of the first audio file during the specified duration. In certain embodiments, the second audio file may comprise a positive-reward cue or a negative-reward cue. In certain embodiments, the audio rendering parameters may comprise parameters for manipulating one or more audio features of the second audio file, wherein the audio rendering parameters are applied to the second audio file at one or more time-points during the specified duration. In accordance with certain aspects of the present disclosure, the audio-processing method may further comprise one or more steps or operations for receiving, with the processor, one or more user-generated inputs for selectively configuring the one or more audio processing parameters, wherein the one or more user-generated inputs comprise one or more inputs for personalizing the therapeutic protocol for the listener. In certain embodiments, the one or more audio rendering parameters may be applied to the first audio file at two or more time-points during the specified duration, wherein the one or more audio rendering parameters are different between a first time-point and a second time-point in the two or more time-points during the specified duration. In certain embodiments, the one or more steps or operations for outputting the acoustic output of the first audio file to the listener for the specified duration may further comprise outputting the acoustic output at two or more separate instances, wherein each instance in the two or more separate instances comprises a separate time interval. In certain embodiments, one or both of the first audio file and the one or more audio rendering parameters may be different between each instance in the two or more separate instances. In accordance with certain aspects of the present disclosure, the audio-processing method may further comprise one or more steps or operations for outputting an acoustic output of a second audio file sequentially or concomitantly with the acoustic output of the first audio file during a second instance in the two or more separate instances.

Further aspects of the present disclosure provide for an audio-processing system for environmental enrichment therapy comprising a loudspeaker; a digital-to-analog converter operably engaged with the loudspeaker; an audio processing device operably engaged with the digital-to-analog converter; and at least one non-transitory computer readable storage medium operably engaged with the audio processing device, the at least one non-transitory computer readable storage medium having processor-executable instructions stored thereon that, when executed, cause the audio processing device to perform one or more operations, the one or more operations comprising: selecting a first audio file from a plurality of audio files according to a therapeutic protocol, wherein the first audio file comprises an audio cue comprising a recorded or artificial sound from an environment; applying one or more audio rendering parameters to the first audio file according to the therapeutic protocol to generate a rendered audio file, wherein the audio rendering parameters comprise parameters for manipulating one or more audio features of the first audio file, wherein the one or more audio features comprise one or more acoustic properties; and outputting, to the digital-to-analog converter operably engaged with the loudspeaker, an acoustic output of the rendered audio file to a listener for a specified duration, wherein the therapeutic protocol comprises parameters for selecting the first audio file from the plurality of audio files and configuring the one or more audio rendering parameters.

Still further aspects of the present disclosure provide for a non-transitory computer readable storage medium having processor-executable instructions stored thereon that, when executed, cause one or more processors to perform one or more operations comprising selecting a first audio file from a plurality of audio files according to a therapeutic protocol, wherein the first audio file comprises an audio cue comprising a recorded or artificial sound from an environment; applying one or more audio rendering parameters to the first audio file according to the therapeutic protocol to generate a rendered audio file, wherein the audio rendering parameters comprise parameters for manipulating one or more audio features of the first audio file, wherein the one or more audio features comprise one or more acoustic properties; and outputting, to a digital-to-analog converter operably engaged with the loudspeaker, an acoustic output of the rendered audio file to a listener for a specified duration, wherein the therapeutic protocol comprises parameters for selecting the first audio file from the plurality of audio files and configuring the one or more audio rendering parameters.

The foregoing has outlined rather broadly the more pertinent and important features of the present invention so that the detailed description of the invention that follows may be better understood and so that the present contribution to the art can be more fully appreciated. Additional features of the invention will be described hereinafter which form the subject of the claims of the invention. It should be appreciated by those skilled in the art that the conception and the disclosed specific methods and structures may be readily utilized as a basis for modifying or designing other structures for carrying out the same purposes of the present invention. It should be realized by those skilled in the art that such equivalent structures do not depart from the spirit and scope of the invention as set forth in the appended claims.

BRIEF DESCRIPTION OF DRAWINGS

The above and other objects, features and advantages of the present disclosure will be more apparent from the following detailed description taken in conjunction with the accompanying drawings, in which.

DETAILED DESCRIPTION

Figure 1:
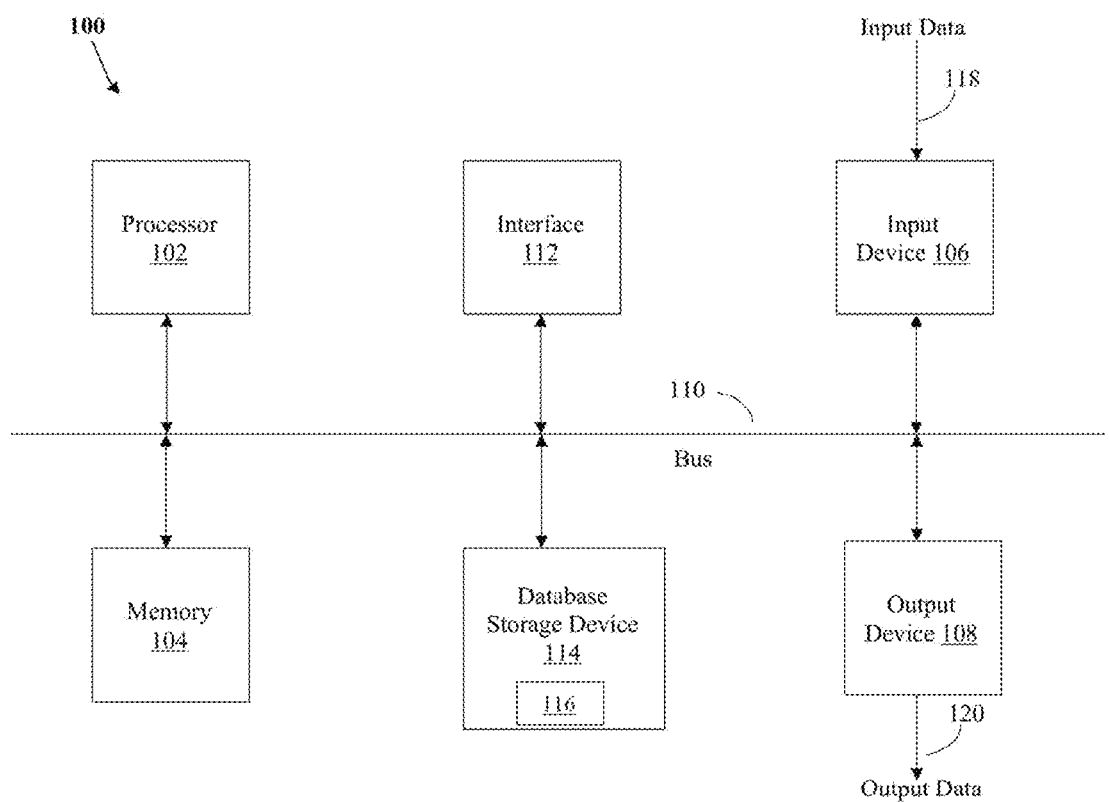
FIG. 1 is an illustrative embodiment of a computing device through which one or more aspects of the present disclosure may be implemented.

It should be appreciated that all combinations of the concepts discussed in greater detail below (provided such concepts are not mutually inconsistent) are contemplated as being part of the inventive subject matter disclosed herein. It also should be appreciated that terminology explicitly employed herein that also may appear in any disclosure incorporated by reference should be accorded a meaning most consistent with the particular concepts disclosed herein.

Following below are more detailed descriptions of various concepts related to, and embodiments of, inventive methods, apparatus and systems configured to process one or more audio file according to one or more audio processing parameters in order to deliver one or more audio-based cues within an environmental enrichment application. In accordance with certain aspects of the present disclosure, the one or more audio processing parameters include parameters for selecting one or more audio file from a bank of audio files comprising a plurality of clinically validated audio cues for one or more CNS disorders, conditions or diseases. In accordance with certain aspects of the present disclosure, the one or more audio processing parameters include parameters for modulating one of more audio characteristics of the one or more audio file, including the speed, pitch, volume, pan, filter cutoff, wavetable index, effects controls, frequency, rhythmicity, wavelength and the like. In accordance with certain aspects of the present disclosure, the one or more audio processing parameters may comprise parameters for combining two or more audio files to render one or more audio-based cues within an environmental enrichment application. Certain aspects of the present disclosure provide for personalization of the one or more audio-based cues within the environmental enrichment application to provide a personalized digital health intervention for at least one patient with one or more CNS disorder, condition or disease.

It should be appreciated that various concepts introduced above and discussed in greater detail below may be implemented in any of numerous ways, as the disclosed concepts are not limited to any particular manner of implementation. Examples of specific implementations and applications are provided primarily for illustrative purposes. The present disclosure should in no way be limited to the exemplary implementation and techniques illustrated in the drawings and described below.

Where a range of values is provided, it is understood that each intervening value, to the tenth of the unit of the lower limit unless the context clearly dictates otherwise, between the upper and lower limit of that range and any other stated or intervening value in that stated range is encompassed by the invention. The upper and lower limits of these smaller ranges may independently be included in the smaller ranges, and are also encompassed by the invention, subject to any specifically excluded limit in a stated range. Where a stated range includes one or both of the endpoint limits, ranges excluding either or both of those included endpoints are also included in the scope of the invention.

As used herein, "exemplary" means serving as an example or illustration and does not necessarily denote ideal or best.

As used herein, the term "includes" means includes but is not limited to, the term "including" means including but not limited to. The term "based on" means based at least in part on.

As used herein, the term "interface" refers to any shared boundary across which two or more separate components of a computer system may exchange information. The exchange can be between software, computer hardware, peripheral devices, humans, and combinations thereof.

As used herein, the term "sound" refers to its common meaning in physics of being an acoustic wave. It therefore also includes frequencies and wavelengths outside of human hearing.

As used herein, the term "signal" refers to any representation of sound whether received or transmitted, acoustic or digital, including an audio cue or other sound source.

As used herein, the term "audio processor" may refer to any apparatus or system configured to electronically manipulate one or more audio signals. An audio processor may be configured as hardware-only, software-only, or a combination of hardware and software.

As used here, the term "cue" means any output or stimuli configured to signal or suggest a user to perform an action or movement of any kind. As used herein, a cue may comprise a plurality of cue modalities, including an audio cue, a haptic cue, a visual cue, an electronic cue, an analog cue, a behavioral cue, olfactory cue and the like.

As used herein, the term "environmental enrichment" may refer to any output or stimuli delivered to a user in any format in order to stimulate the brain of the user. In accordance with certain aspects of the present disclosure, environmental enrichment may comprise the delivery of one or more cues to the user.

An exemplary system, method, and apparatus according to the principles herein may include an environmental enrichment platform and application configured to deliver at least one clinically-validated cue or combination of cues to a user in order to provide a therapeutic effect to at least one symptom or aspect of a CNS disease, disorder or condition, including underlying drivers of such diseases, disorders and/or conditions. In accordance with certain aspects of the present disclosure, the at least one clinically-validated cue or combination of cues comprises an audio cue.

In accordance with an exemplary use case provided by embodiments of the present disclosure, a user of an environmental enrichment platform and application may instantiate an instance of the environmental enrichment application on at least one user device (e.g., a smart phone). The instance of the environmental enrichment application may be configured to present a one or more cues to the user during a specified duration. The one or more cues may be personalized to the user based on one or more parameters that are preconfigured or dynamically tailored to the user. The user may receive the one or more cues across one or more sessions of the environmental enrichment application as therapy for at least one symptom or aspect of a CNS disease, disorder or condition.

Certain benefits and advantages of the present disclosure include an audio-processing method and system for providing personalized and dynamic audio cues to at least one user within an environmental enrichment platform and application. Certain benefits and advantages over the prior art include novel audio processing and rendering methods for outputting one or more audio files comprising one or more audio cues, including combinations of audio files and combinations of audio cues, to the at least one user.

Turning now descriptively to the drawings, in which similar reference characters denote similar elements throughout the several views, FIG. 1 depicts an exemplary computing system in which certain illustrated embodiments of the present invention may be implemented.

Referring now to FIG. 1, a processor-implemented computing device in which one or more aspects of the present disclosure may be implemented is shown. According to an embodiment, a processing system 100 may generally comprise at least one processor 102, or processing unit or plurality of processors, memory 104, at least one input device 106 and at least one output device 108, coupled together via a bus or group of buses 110. In certain embodiments, input device 106 and output device 108 could be the same device. An interface 112 can also be provided for coupling the processing system 100 to one or more peripheral devices, for example interface 112 could be a PCI card or PC card. At least one storage device 114 which houses at least one database 116 can also be provided. The memory 104 can be any form of memory device, for example, volatile or non-volatile memory, solid state storage devices, magnetic devices, etc. The processor 102 could comprise more than one distinct processing device, for example to handle different functions within the processing system 100. Input device 106 receives input data 118 and can comprise, for example, a keyboard, a pointer device such as a pen-like device or a mouse, audio receiving device for voice-controlled activation such as a microphone, data receiver or antenna such as a modem or wireless data adaptor, data acquisition card, etc. Input data 118 could come from different sources, for example keyboard instructions in conjunction with data received via a network. Output device 108 produces or generates output data 120 and can comprise, for example, a display device or monitor in which case output data 120 is visual, a printer in which case output data 120 is printed, a port for example a USB port, a peripheral component adaptor, a data transmitter or antenna such as a modem or wireless network adaptor, etc. Output data 120 could be distinct and derived from different output devices, for example a visual display on a monitor in conjunction with data transmitted to a network. A user could view data output, or an interpretation of the data output, on, for example, a monitor or using a printer. The storage device 114 can be any form of data or information storage means, for example, volatile or non-volatile memory, solid state storage devices, magnetic devices, etc.

In use, the processing system 100 is adapted to allow data or information to be stored in and/or retrieved from, via wired or wireless communication means, at least one database 116. The interface 112 may allow wired and/or wireless communication between the processing unit 102 and peripheral components that may serve a specialized purpose. In general, the processor 102 can receive instructions as input data 118 via input device 10a and can display processed results or other output to a user by utilizing output device 108. More than one input device 106 and/or output device 108 can be provided. It should be appreciated that the processing system 100 may be any form of terminal, server, specialized hardware, or the like.

It is to be appreciated that the processing system 100 may be a part of a networked communications system. Processing system 100 could connect to a network, for example the Internet or a WAN. Input data 118 and output data 120 could be communicated to other devices via the network. The transfer of information and/or data over the network can be achieved using wired communications means or wireless communications means. A server can facilitate the transfer of data between the network and one or more databases. A server and one or more databases provide an example of an information source.

Thus, the processing computing system environment 100 illustrated in FIG. 1 may operate in a networked environment using logical connections to one or more remote computers. The remote computer may be a personal computer, a server, a router, a network PC, a peer device, or other common network node, and typically includes many or all of the elements described above.

It is to be further appreciated that the logical connections depicted in FIG. 1 include a local area network (LAN) and a wide area network (WAN) but may also include other networks such as a personal area network (PAN). Such networking environments are commonplace in offices, enterprise-wide computer networks, intranets, and the Internet. For instance, when used in a LAN networking environment, the computing system environment 100 is connected to the LAN through a network interface or adapter. When used in a WAN networking environment, the computing system environment typically includes a modem or other means for establishing communications over the WAN, such as the Internet. The modem, which may be internal or external, may be connected to a system bus via a user input interface, or via another appropriate mechanism. In a networked environment, program modules depicted relative to the computing system environment 100, or portions thereof, may be stored in a remote memory storage device. It is to be appreciated that the illustrated network connections of FIG. 1 are exemplary and other means of establishing a communications link between multiple computers may be used.

FIG. 1 is intended to provide a brief, general description of an illustrative and/or suitable exemplary environment in which embodiments of the below described present invention may be implemented. FIG. 1 is an example of a suitable environment and is not intended to suggest any limitation as to the structure, scope of use, or functionality of an embodiment of the present invention. A particular environment should not be interpreted as having any dependency or requirement relating to any one or combination of components illustrated in an exemplary operating environment. For example, in certain instances, one or more elements of an environment may be deemed not necessary and omitted. In other instances, one or more other elements may be deemed necessary and added.

In the description that follows, certain embodiments may be described with reference to acts and symbolic representations of operations that are performed by one or more computing devices, such as the computing system environment 100 of FIG. 1. As such, it will be understood that such acts and operations, which are at times referred to as being computer-executed, include the manipulation by the processor of the computer of electrical signals representing data in a structured form. This manipulation transforms the data or maintains them at locations in the memory system of the computer, which reconfigures or otherwise alters the operation of the computer in a manner understood by those skilled in the art. The data structures in which data is maintained are physical locations of the memory that have particular properties defined by the format of the data. However, while an embodiment is being described in the foregoing context, it is not meant to be limiting as those of skill in the art will appreciate that the acts and operations described hereinafter may also be implemented in hardware.

Embodiments may be implemented with numerous other general-purpose or special-purpose computing devices and computing system environments or configurations. Examples of well-known computing systems, environments, and configurations that may be suitable for use with an embodiment include, but are not limited to, personal computers, handheld or laptop devices, personal digital assistants, multiprocessor systems, microprocessor-based systems, set top boxes, programmable consumer electronics (such as smartphones, tablet computers, personal computers and the like), network, minicomputers, server computers, game server computers, web server computers, mainframe computers, and distributed computing environments that include any of the above systems or devices.

Embodiments may be described in a general context of computer-executable instructions, such as program modules, being executed by a computer. Generally, program modules include routines, programs, objects, components, data structures, etc., that perform particular tasks or implement particular abstract data types. An embodiment may also be practiced in a distributed computing environment where tasks are performed by remote processing devices that are linked through a communications network. In a distributed computing environment, program modules may be located in both local and remote computer storage media including memory storage devices.

With the exemplary computing system environment 100 of FIG. 1 being generally shown and discussed above, description will now turn towards illustrated embodiments of the present invention which generally relates to methods for selecting at least one audio file comprising a clinically-validated audio cue from a plurality of audio files comprising a plurality of clinically-validated audio cues, applying one or more audio rendering parameters to the at least one audio file, and outputting an acoustic output of the first audio file to a user for a specified duration.

Before the present invention and specific exemplary embodiments of the invention are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, exemplary methods and materials are now described. All publications mentioned herein are incorporated herein by reference to disclose and describe the methods and/or materials in connection with which the publications are cited.

It must be noted that as used herein and in the appended claims, the singular forms "a", "an," and "the" include plural referents unless the context clearly dictates otherwise. Thus, for example, reference to "a stimulus" includes a plurality of such stimuli and reference to "the signal" includes reference to one or more signals and equivalents thereof known to those skilled in the art, and so forth.

Any publications discussed herein are provided solely for their disclosure prior to the filing date of the present application. Nothing herein is to be construed as an admission that the present invention is not entitled to antedate such publication by virtue of prior invention. Further, the dates of publication provided may differ from the actual publication dates which may need to be independently confirmed.

Figure 2:
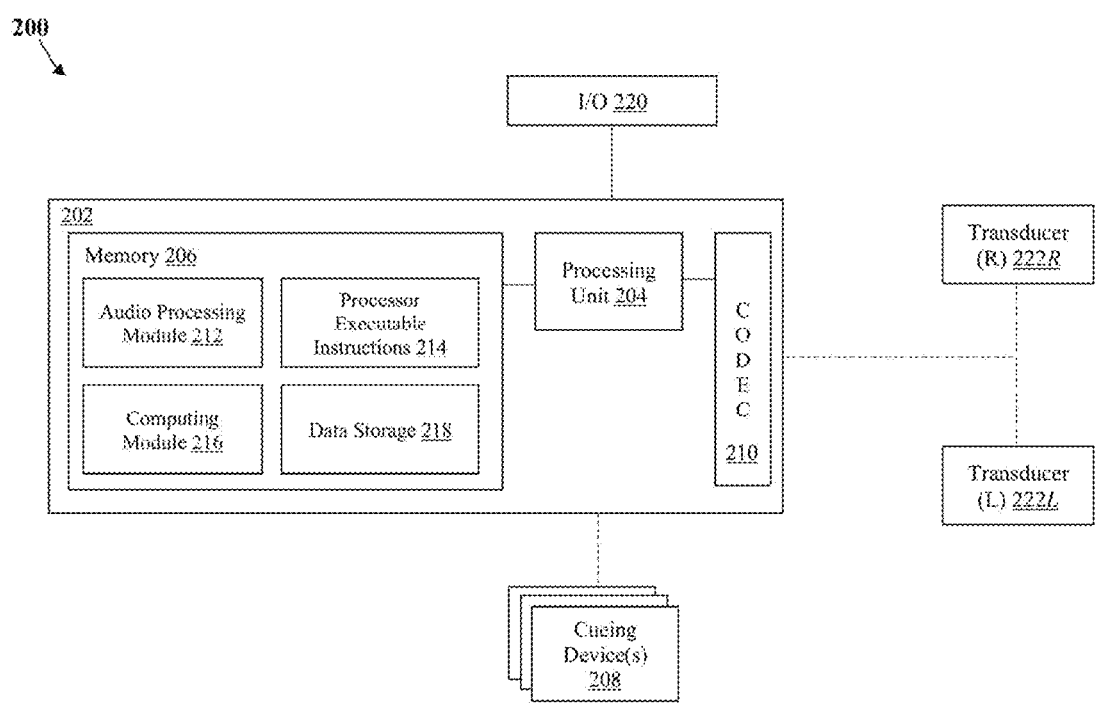
FIG. 2 is an illustrative embodiment of a computing system through which one or more aspects of the present disclosure may be implemented.

Referring now to FIG. 2, an illustrative embodiment of a computing system 200 through which one or more aspects of the present disclosure may be implemented is shown. In accordance with an embodiment, computing system 200 is comprised of a computing device 202 being communicably engaged with transducers 222R and 222L. In certain embodiments, computing device 202 is operably engaged with an input/output (I/O) device 220. Computing device 202 may be operably comprised of a processing unit 204, a memory 206, one or more sensors 208, and an audio codec 210. In certain embodiments, computing device 202 may be embodied as the exemplary computing system environment 100 of FIG. 1. Memory 206 may comprise a plurality of modules comprising instructions to cause processing unit 204 to perform certain functions and operations in accordance with an audio processing method and system for environmental enrichment therapy. In accordance with an embodiment, memory 206 may comprise an audio processing module 212, processor executable instructions 214, a computing module 216, and data storage 218. Audio processing module 212 may comprise certain audio processing software that enables the processor to perform one or more audio processing functions. Audio processing module 212 may comprise one or more audio signal processing functions comprising an audio mixing function, an audio effects function, an audio rendering function, and an audio output function. Audio processing module 212 may comprise one or more software-based modulators comprising control parameters for manipulating one or more characteristics of a target signal or carrier, such as effects, spectral modulation and/or sequencing. Audio processing module 212 may be configured to route a modulation source to modulate pitch, volume, pan, filter cutoff, wavetable index, effects controls, frequency, rhythmicity, and wavelength. In accordance with certain embodiments, one or more software-based modulators may comprise one or more of a low frequency oscillator, an ADSR envelope, a modulation wheel, and a step sequencer. Audio processing module 212 may comprise instructions for processing and rendering one or more audio sequences. In accordance with certain embodiments, an audio sequence may be generated through the application of a modulator function, such as a step sequencer module, or a signal generator function, such as a random sequence generator or MIDI generator. A step sequencer or signal generator function may comprise one or more control parameters that may be dynamically configured by computing module 216. Audio processing module 212 may comprise a spectral effects module configured to modulate the distribution of a sound signal in a stereo field and/or other spatial effects.

Computing module 216 may comprise application logic for executing an audio interference processing application on one or more computing devices. Computing module 216 may comprise instructions for controlling one or more audio processing functions of audio processing module 212, including instructions for dynamically controlling one or more audio processing functions. Computing module 216 may generally provide instructions for configuring one or more audio interference process controls, processing sensor inputs, and dynamically modifying one or more application or audio processing control parameters. Processor executable instructions 214 may be dynamically modified or informed by one or more control parameters of computing module 216, and may comprise instructions to enable processing unit 204 to execute a plurality of operations in an audio processing method comprising selecting a first audio file from a plurality of audio files; applying one or more audio rendering parameters to the first audio file; and outputting, to CODEC 210, an acoustic output of the first audio file for a specified duration. In accordance with certain aspects of the present disclosure, processor executable instructions 214 may comprise instructions to enable processing unit 204 to execute a plurality of operations in an audio processing method comprising selecting a second audio file from the plurality of audio files, wherein the second audio file comprises a recording of a different audio cue from the first audio file. Processor executable instructions 214 may further comprise instructions to enable processing unit 204 to execute a plurality of operations in an audio processing method comprising outputting, to CODEC 210, an acoustic output of the second audio file sequentially or concomitantly with the acoustic output of the first audio file during the specified duration. In accordance with certain embodiments, the second audio file comprises a positive-reward cue or a negative-reward cue. In accordance with certain embodiments, the audio rendering parameters comprise parameters for manipulating one or more audio features of the second audio file; e.g., at one or more timepoints during the specified duration. Processor executable instructions 214 may further comprise instructions to enable processing unit 204 to execute a plurality of operations in an audio processing method comprising receiving one or more user-generated inputs for selectively configuring the one or more audio processing parameters. Processor executable instructions 214 may further comprise instructions to enable processing unit 204 to execute a plurality of operations in an audio processing method comprising outputting an acoustic output of a second audio file sequentially or concomitantly with the acoustic output of the first audio file during a second instance in the two or more separate instances.

Data storage 218 may be operable to store application controls, application data, and audio files, and may comprise one or more databases. Cueing device(s) 208 may comprise one or more wearable electronic device, such as a smart watch or activity tracker; smart glasses, including AR/VR glasses or goggles and other head-ups displays; headphones, loudspeakers/speakers or other audio transducers; smartphone or personal computing device with at least one output device; and one or more health device, optionally including one or more wearable physiological sensors. In certain embodiments, I/O device 220 may also comprise one or more touch sensors or motion sensors, such as capacitive MEMS accelerometers, piezoresistive accelerometers, and piezoelectric accelerometers, gyroscope, e-compass, 5-wire (or 4-wire) resistive sensors, surface capacitive sensors, projected capacitive sensors, surface acoustic wave sensors, and infrared sensors, and the like.

Codec 210 may be a hardware audio codec operable to execute a digital-to-analog conversion of audio cueing signals and output to transducers 222R and 222L. In certain embodiments, codec 210 may be substituted for a digital-to-analog converter or may comprise a digital-to-analog converter. Transducers 222R and 222L may comprise any type of acoustic transducer operable to output an acoustic soundwave. In certain embodiments, transducer 222R is embodied as a right speaker in a stereo field, and transducer 222L is embodied as a left speaker in a stereo sound field. In certain embodiments, transducers 222R and 222L are embodied as a pair of headphones. In other embodiments, computing system 200 may be comprised of a single transducer 222 in a monaural sound field. Alternatively, computing system 200 may be comprised of three or more transducers 222 operating in a stereophonic sound field between 180 and 360 degrees.

In certain embodiments, computing device 202 may comprise a smart phone or a tablet computer. In such embodiments, I/O device 220 may be configured as a touch screen display and integrally configured with computing device 202. I/O device 220 may further comprise an external input device, such as a mouse, joystick, gaming controller, and the like. I/O device 220 may be comprised of multiple input devices comprising multiple input modalities, such as one or more video cameras, microphones, wearable sensors, and touch screen interfaces; and, multiple output devices, such as one or more visual displays, audio speakers, and haptic output devices, such as wearable electronic devices. In certain embodiments, computing device 202 may be embodied in a completely audio-based format, such that I/O device 220 comprises one or more acoustic transducers comprising a microphone input and an audio speaker output.

Figure 3:
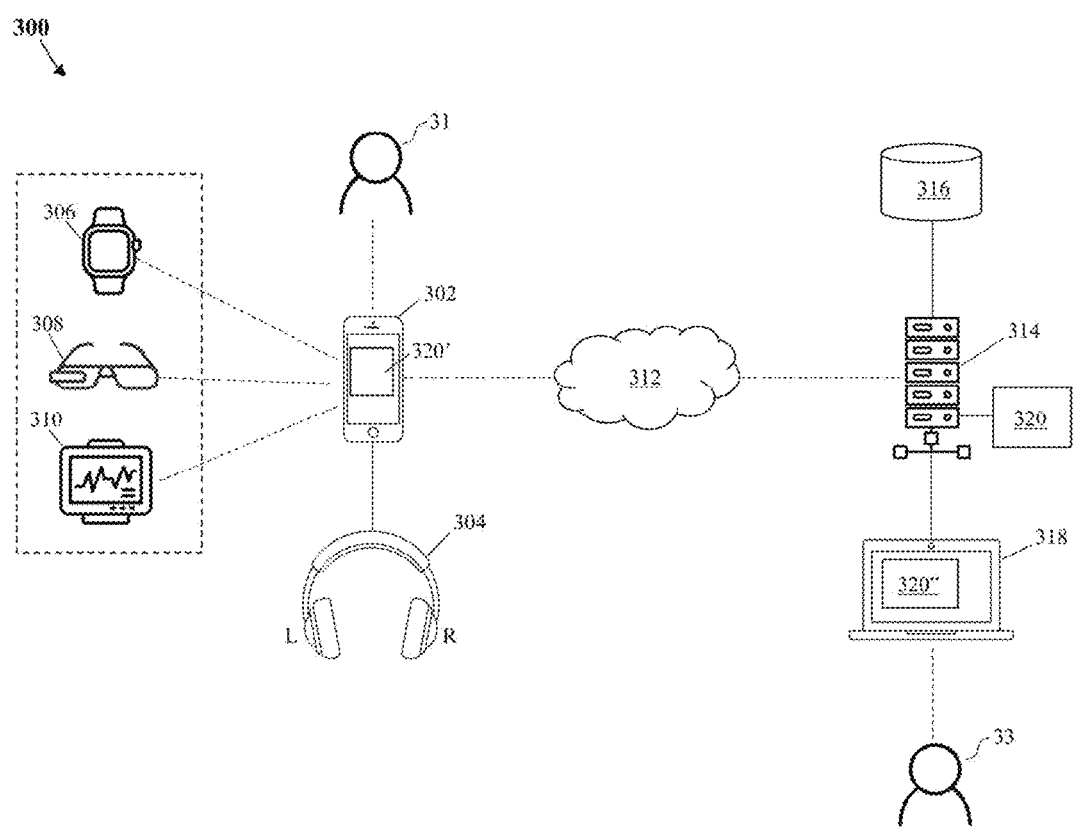
FIG. 3 is an illustrative embodiment of a system architecture through which one or more aspects of the present disclosure may be implemented.

Referring now to FIG. 3, an illustrative embodiment of a system architecture through which one or more aspects of the present disclosure may be implemented is shown. In accordance with certain aspects of the present disclosure, an audio processing system 300 may comprise at least one end-user device 302, an application server 314 communicably engaged with end-user device 302 via a communication network 312, an audio database 316 communicably engaged with application server 314, and at least one client device 318 communicably engaged with application server 314. In accordance with certain aspects of the present disclosure, audio processing system 300 may comprise exemplary computing system environment 100 of FIG. 1 and/or exemplary computing system 200 of FIG. 2. Audio processing system 300 may further comprise at least one set of speakers 304 operably engaged with end-user device 302. In certain embodiments, speakers 304 may comprise a right transducer and a left transducer configured to produce a stereo audio output. In certain embodiments, speakers 304 may comprise one or more body-worn speakers, such as ear pods or eyeglasses with one or more integrated transducers. Client device 318 may comprise a mobile computing device, such as a smart phone, tablet computer or personal digital assistant device. In accordance with certain embodiments, audio processing system 300 may comprise one or more auxiliary cueing device, including a wearable electronic device 306 (e.g., smart watch or activity tracker device), smart glasses 308 (e.g., such as augmented reality (AR) glasses or virtual reality (VR) goggles), and one or more personal health monitoring device 310 (e.g., a heart monitoring device, a fall-monitoring device, an activity tracker with one or more integrated physiological sensors, and/or a smart watch with one or more physiological sensors).

In accordance with certain aspects of the present disclosure, application server 314 may comprise an environmental enrichment application 320 being hosted thereon. End user device 302 may comprise an end user instance 320' of environmental enrichment application 320. In accordance with certain aspects of the present disclosure, an end user 31 may launch an instance 320' of environmental enrichment application 320 at end user device 302. End user device 302 may communicate server call to application server 314 and application server 314 may instantiate an instance of environmental enrichment application 320 at application server 314. In accordance with certain aspects of the present disclosure, environmental enrichment application 320 may be configured to provide one or more environmental cues via end user instance 320' to end user 31 during a session. In certain embodiments, the one or more environmental cues are clinically validated cues configured to treat at least one aspect of a CNS disorder, condition or disease; for example, freezing of gait associated with Parkinson's disease. In certain embodiments, the one or more environmental cues comprise one or more audio files comprising a recorded or artificial sound from a natural or artificial environment; for example, a recording of a person walking in gravel, a recording of a person walking down a corridor in soled shoes, a person walking in flip-flops, a person walking in a forest, a bell, a synthesizer, the sound of a motor starting up, the sound of footsteps in a natural (e.g., forest or gravel path) or artificial (e.g., an interior corridor such as a hallway) environment setting, etc. In certain embodiments, the one or more environmental cues comprise one or more haptic, visual and/or audible output from one or more of wearable electronic device 306, smart glasses 308 and/or personal health monitoring device 310.

In accordance with certain aspects of the present disclosure, end user instance 320' may comprise a therapeutic session during which a plurality of environmental cues is presented to end user 31 for a specified duration in accordance with a plurality of cue parameters. In accordance with certain aspects of the present disclosure, the plurality of cue parameters may comprise one or more audio processing parameters. In certain embodiments, the one or more audio processing parameters may comprise one or more audio processing algorithms configured select one or more audio files from a plurality of audio files stored in audio database 316 and apply one or more rendering/processing parameters to the one or more audio files to generate an audio output that is personalized for end user 31. The one or more audio processing algorithms may also include one or more operations for configuring cues from the one or more auxiliary cueing devices; e.g., wearable electronic device 306, smart glasses 308 and/or personal health monitoring device 310. In accordance with certain aspects of the present disclosure, the one or more audio processing algorithms may be configured, tailored and/or modified by an admin user 33 via an admin user instance 320" of environmental enrichment application 320 executing on client device 318. Admin user 33 may be a health care provider, such as a doctor, a physical therapist, a neurologist, a nurse, etc. In accordance with certain embodiments, admin user 33 may comprise the same user as end user 31 (i.e., the same user may be assigned both user roles in environmental enrichment application 320). In accordance with such embodiments, environmental enrichment application 320 may be configured to enable end user 31 to configure, tailor and/or modify the one or more audio processing algorithms and/or the plurality of audio files stored in audio database 316.

In accordance with certain aspects of the present disclosure, environmental enrichment application 320 may comprise one or more algorithms for assembling and delivering one or more environmental cues for treating one or more CNS disorders, diseases or conditions. In accordance with certain embodiments, at least one algorithm in the one or more algorithms may be expressed as follows:

$$y(\text{Disease}) = a^* cue_1^n + b^* cue_2^{n2} + \ldots + c^* reward_1^x +$$

or, $$y(\text{Disease}) = a^* cue_1 + b^* cue_2 + \ldots + reward1_1 + reward_2 +$$

or, $$y(\text{Disease}) = f(cue1, \ldots, cueN, reward1, \ldots, rewardN)$$

In accordance with the above, y(Disease) may comprise the treatment form or algorithm that emerges from the combination of cues to address the CNS disorder, disease or condition; for example, freezing of gait associated with Parkinson's Disease. In accordance with the above, Disease is defined as the entire disorder or a facet/aspect/symptom/manifestation, or any disease attribute, of a disorder for which one would seek to develop a therapeutic intervention; for example, Disease here could represent Parkinson's Disease or motor dysfunction, imbalance, or freezing of gait that is characteristic of various aspects of a disease involving motor dysfunction.

In accordance with the above, a cue may represent any cueing modality for which environmental enrichment application 320 is configured to output; e.g., auditory, visual, electric, haptic, behavioral, etc. In accordance with certain aspects of the present disclosure, cues may be presented individually or in combination with other cues. Additionally, various attributes (sub-features) with regard to a single cue may also be manipulated to create a combinatorial cue delivery for therapeutic intervention; for example, manipulating acoustic properties of an audio cue such as the speed, volume, pitch, interval/frequency, pan, and the like. This changing of parameters is what is represented by a, b, and c in the above equations. Collectively these cues might represent a model of understanding to admin user 33 for manipulating human function in a normal and disease state.

Figure 4:
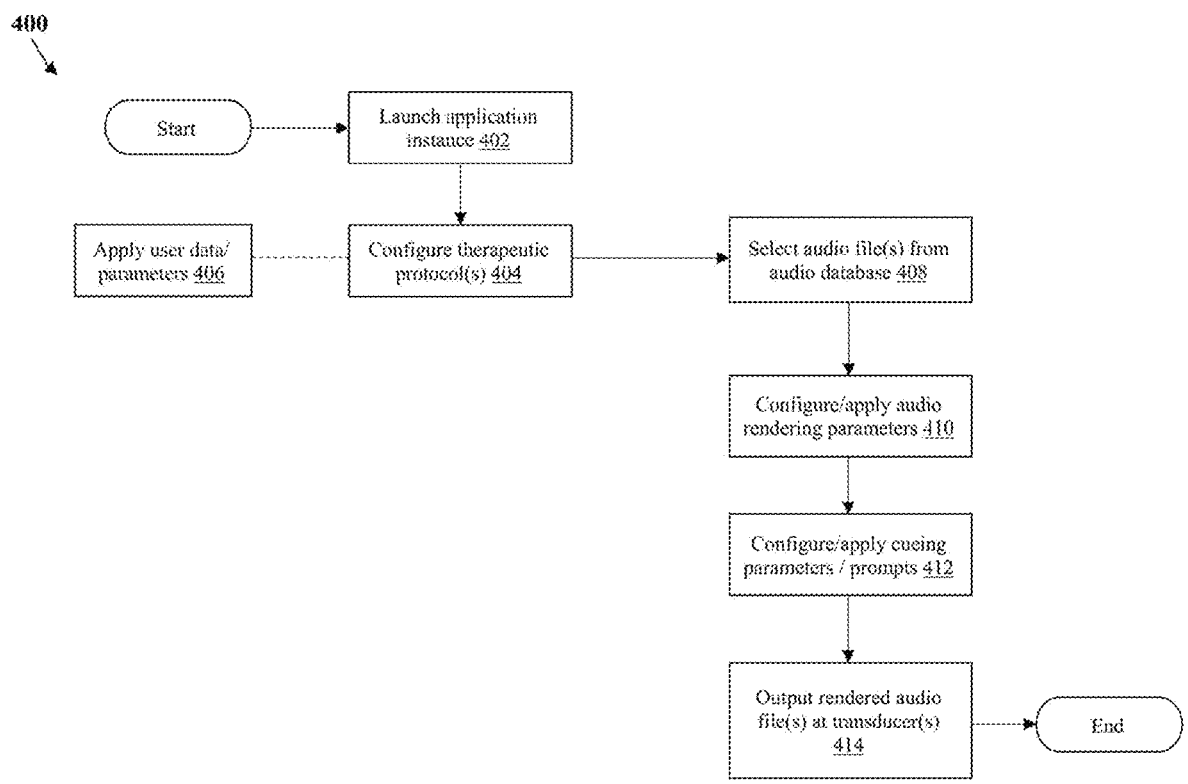
FIG. 4 is a functional block diagram of a routine of an audio processing system for environmental enrichment therapy, in accordance with certain aspects of the present disclosure.

Referring now to FIG. 4, a functional block diagram of a routine 400 of an audio processing system for environmental enrichment therapy is shown. In accordance with certain aspects of the present disclosure, the audio processing system for environmental enrichment therapy may comprise system 300 of FIG. 3. In accordance with certain embodiments, routine 400 may comprise one or more processor-executable instructions executed on exemplary computing system environment 100 of FIG. 1 and/or exemplary computing system 200 of FIG. 2. In accordance with certain aspects of the present disclosure, routine 400 may comprise one or more steps or operations for launching an instance of an environmental enrichment application at an end user device (Step 402). In certain embodiments, the instance of the environmental enrichment application may comprise end user instance 320' of environmental enrichment application 320, as shown in FIG. 3. Routine 400 may continue by performing one or more steps or operations for configuring one or more therapeutic protocols for the environmental enrichment application (Step 404). In certain embodiments, the one or more therapeutic protocols may comprise one or more protocols for configuring and delivering one or more environmental cues to an end user. In certain embodiments, Step 404 may comprise one or more steps or operations for applying a plurality of user data and/or user parameters 406 for personalizing the one or more environmental cues for the end user across one or more sessions of the environmental enrichment application. Routine 400 may proceed by performing one or more operations for selecting one or more audio files from an audio database comprising a plurality of audio files (Step 408). In accordance with certain embodiments, the one or more audio files may comprise one or more clinically-validated audio cues for treating at least one CNS disorder, disease or condition. In accordance with certain embodiments, the one or more audio files are selected in Step 408 in accordance with the configured therapeutic protocols from Step 404. Routine 400 may continue by performing one or more steps or operations for configuring and applying one or more audio rendering parameters to the one or more audio files (Step 410). In accordance with certain embodiments, the one or more rendering parameters are configured to manipulate one or more acoustic properties of the one or more audio files; for example, speed, pitch, volume, pan, filter cutoff, wavetable index, effects controls, frequency, rhythmicity, wavelength and the like. Routine 400 may proceed by executing one or more steps or operations for configuring and applying one or more cueing parameters and/or prompts to the one or more audio files (Step 412). For example, the one or more cueing parameters and/or prompts may comprise parameters for timing of delivery of a cue, duration of a cue, termination of a cue, etc. Routine 400 may conclude by performing one or more steps or operations for outputting a rendered audio file comprising the final assembled output of Steps 408-412 at one or more transducers (Step 414). In accordance with certain embodiments, the one or more transducers may comprise one or more speakers operably engaged with an end user device.

Figure 5:
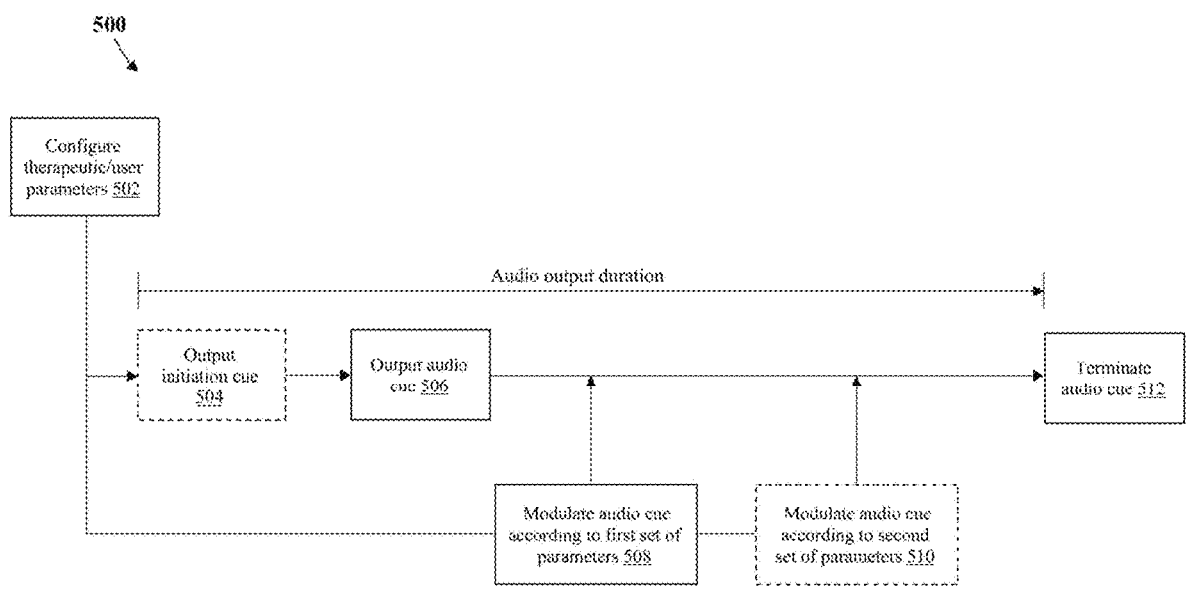
FIG. 5 is a functional block diagram of a routine of an audio processing system for environmental enrichment therapy, in accordance with certain aspects of the present disclosure.

Referring now to FIG. 5, a functional block diagram of a routine 500 of an audio processing system for environmental enrichment therapy is shown. In accordance with certain aspects of the present disclosure, the audio processing system for environmental enrichment therapy may comprise system 300 of FIG. 3. In accordance with certain embodiments, routine 500 may comprise one or more processor-executable instructions executed on exemplary computing system environment 100 of FIG. 1 and/or exemplary computing system 200 of FIG. 2. In accordance with certain aspects of the present disclosure, routine 500 may be successive or sequential to one or more steps or operations of routine 400 of FIG. 4 and/or may comprise one or more sub-steps or sub-routines of routine 400 of FIG. 4.

In accordance with certain aspects of the present disclosure, routine 500 may be configured to perform one or more steps or operations for presenting at least one audio cue to an end user for a specified duration. In accordance with certain embodiments, routine 500 may comprise one or more steps or operations for configuring one or more therapeutic parameters or user-specific parameters for at least one audio file comprising at least one audio cue (Step 502). In accordance with certain embodiments, the at least one audio file may comprise an output of routine 400, as shown in FIG. 4. Routine 500 may optionally comprise one or more steps or operations for outputting an initiation cue to one or more transducers operably engaged with an end user device (Step 504). The initiation cue may comprise a cue configured to prompt an end user to take a specified action (e.g., stand up) or otherwise notify the user that an audio cue is soon to be delivered. In accordance with certain aspects of the present disclosure, the initiation cue may be initiated by the end user (e.g., in response to a user-generated input via a user interface of the environmental enrichment application). In accordance with certain aspects of the present disclosure, the initiation cue comprises one or more breathing prompts. In certain embodiments, the breathing prompts may comprise a breath routine that the user is prompted or required to complete before routine 500 proceeds. The one or more breathing prompts may be configured as audio prompts and may comprise a voice-prompt (e.g., "take 5 deep breaths") or an action-relevant cue such as a recording of a person breathing or other environmental cue such as the sound of wind or moving air. The initiation cue may be output for a specified duration before routine 500 proceeds. Routine 500 may continue by performing one or more steps or operations for outputting the audio cue to the one or more transducers (Step 506). In accordance with certain aspects of the present disclosure, routine 500 may comprise one or more steps or operations for modulating the audio cue according to a first set of parameters at a first timepoint during the audio output duration (Step 508). The first set of parameters may comprise one or more parameters for modulating one or more acoustic properties of the audio cue, such as speed, pitch, volume, pan, filter cutoff, wavetable index, effects controls, frequency, rhythmicity, wavelength and the like. In certain embodiments, the first set of parameters may comprise one or more parameters for changing the audio cue; for example, from a first audio cue (e.g., a recording of a person walking on a gravel path) to a second audio cue (e.g., a recording of a person walking in hard-soled shoes in an interior corridor). In accordance with certain embodiments, one or both of the first audio cue and/or the second audio cue may comprise a discrete cue (e.g., a metronome, the sound of a person walking in soled shoes in an interior corridor or the like) and/or one or both of the first audio cue and/or the second audio cue may comprise a continuous cue (e.g., the sound of a person walking on a gravel path or other continuous audio cue, such as from a natural environment like walking in a forest). In accordance with certain embodiments, routine 500 may optionally comprise one or more steps or operations for modulating the audio cue according to a second set of parameters at a second or subsequent timepoint during the audio output duration (Step 510). In certain embodiments, the second set of parameters may be different from the first set of parameters; i.e., the second set of parameters may manipulate the audio cue in a different way than that of the first set of parameters. The second set of parameters may comprise one or more parameters for modulating one or more acoustic properties of the audio cue, such as speed, pitch, volume, pan, filter cutoff, wavetable index, effects controls, frequency, rhythmicity, wavelength and the like. In certain embodiments, the second set of parameters may comprise one or more parameters for changing the audio cue; for example, from a first audio cue (e.g., a recording of a person walking on a gravel path) to a second audio or subsequent audio cue (e.g., a recording of a person walking in hard-soled shoes in an interior corridor). In accordance with certain aspects of the present disclosure, routine 500 may conclude by executing one or more steps or operations for terminating the audio cue at the conclusion of the audio output duration (Step 512).

Figure 6:
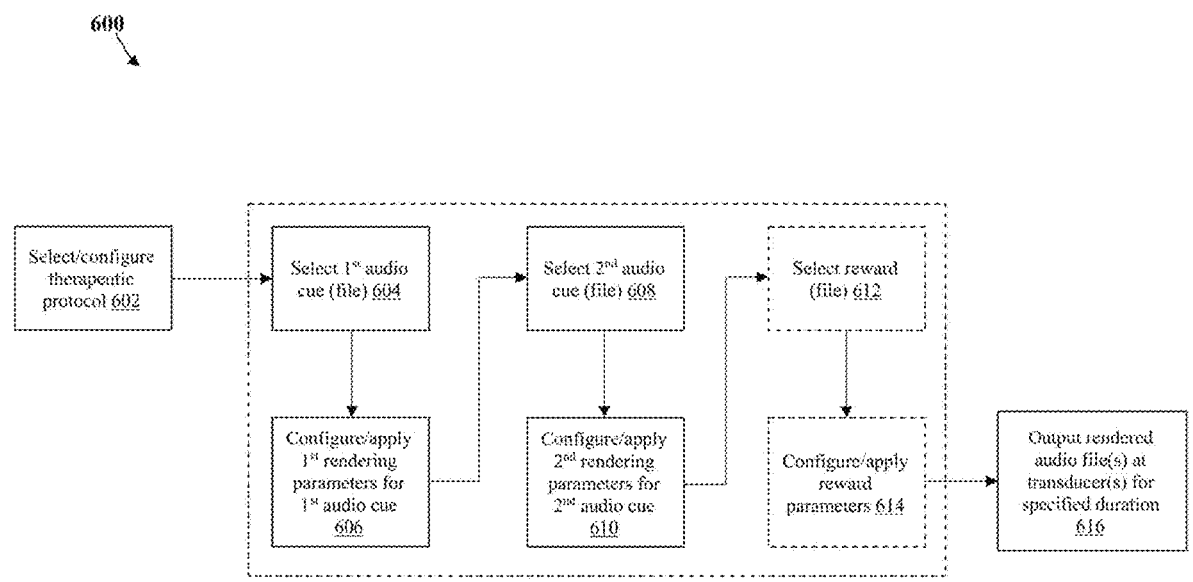
FIG. 6 is a functional block diagram of a routine of an audio processing system for environmental enrichment therapy, in accordance with certain aspects of the present disclosure.

Referring now to FIG. 6, a functional block diagram of a routine 600 of an audio processing system for environmental enrichment therapy is shown. In accordance with certain aspects of the present disclosure, the audio processing system for environmental enrichment therapy may comprise system 300 of FIG. 3. In accordance with certain embodiments, routine 600 may comprise one or more processor-executable instructions executed on exemplary computing system environment 100 of FIG. 1 and/or exemplary computing system 200 of FIG. 2. In accordance with certain aspects of the present disclosure, routine 600 may be successive or sequential to one or more steps or operations of routines 400-500 of FIGS. 4-5 and/or may comprise one or more sub-steps or sub-routines of routines 400-500 of FIGS. 4-5.

In accordance with certain aspects of the present disclosure, routine 600 may comprising one or more steps or operations for selecting and/or configuring a therapeutic protocol within an environmental enrichment application (Step 602). In accordance with certain embodiments, the therapeutic protocol may comprise parameters for delivering one or more environmental cues comprising one or more cueing modalities to an end user via one or more end user device. In certain embodiments, an environmental cue comprises a clinically validated audio cue. Routine 600 may proceed by performing one or more steps or operations for selecting a first audio file comprising a first audio cue from a plurality of audio files in an audio database (Step 604). Routine 600 may proceed by executing one or more steps or operations for configuring and applying a first set of rendering parameters for the first audio cue (Step 606). In accordance with certain embodiments, the first set of rendering parameters comprises one or more parameters for manipulating one or more acoustic properties of the first audio cue, such as speed, pitch, volume, pan, filter cutoff, wavetable index, effects controls, frequency, rhythmicity, wavelength and the like. The first set of rendering parameters may also comprise one or more parameters for timing of presentation and duration of the first audio cue. Routine 600 may proceed by executing one or more steps or operations for selecting a second audio cue from the plurality of audio files in an audio database (Step 608). In accordance with certain embodiments, the second audio cue comprises a different audio cue from that of the first audio cue. Routine 600 may comprise one or more steps or operations for configuring and applying a second set of rendering parameters for the second audio cue (Step 610). In accordance with certain embodiments, the second set of rendering parameters may be different than the first set of rendering parameters or may be the same as the first set of rendering parameters. The second set of rendering parameters may comprise one or more parameters for manipulating one or more acoustic properties of the second audio cue, such as speed, pitch, volume, pan, filter cutoff, wavetable index, effects controls, frequency, rhythmicity, wavelength and the like. The second set of rendering parameters may also comprise one or more parameters for timing of presentation and duration of the second audio cue relative to the first audio cue. In accordance with certain aspects of the present disclosure, routine 600 may comprise one or more steps or operations for selecting at least one reward file (Step 612). In accordance with certain embodiments, the at least one reward file may comprise a positive reward or a negative reward to be delivered either sequentially or concomitantly with the first audio cue and/or the second audio cue. In certain embodiments, the reward file may comprise an audio prompt or notification configured to indicate to the user that a reward has been achieved/delivered. The reward file may be configured to reinforce neuronal changes in the end user driven by the presentation of the first audio cue and the second audio cue. Examples of positive reward cues may comprise a points-based system, visual rewards, monetary rewards, charitable contributions, "virtual points" to be used for rewards such as merchandise, experiential, gamification, and social interactions. In accordance with certain aspects of the present disclosure, the reward may be delivered to the user within a graphical user interface of an end user application. Routine 600 may continue by performing one or more steps or operations for configuring one or more reward parameters (Step 614). In accordance with certain embodiments, the one or more reward parameters may comprise parameters for timing/delivery of a reward cue, the conditions for receiving a reward and the parameters for delivering one or more reward asset to the end user. Routine 600 may conclude by outputting one or more rendered audio files to at least one transducer operably engaged with the end user device for a specified duration (Step 616). In accordance with certain aspects of the present disclosure, an output of step 616 comprises a therapeutic delivery session within an instance of the end user application.

Figure 7:
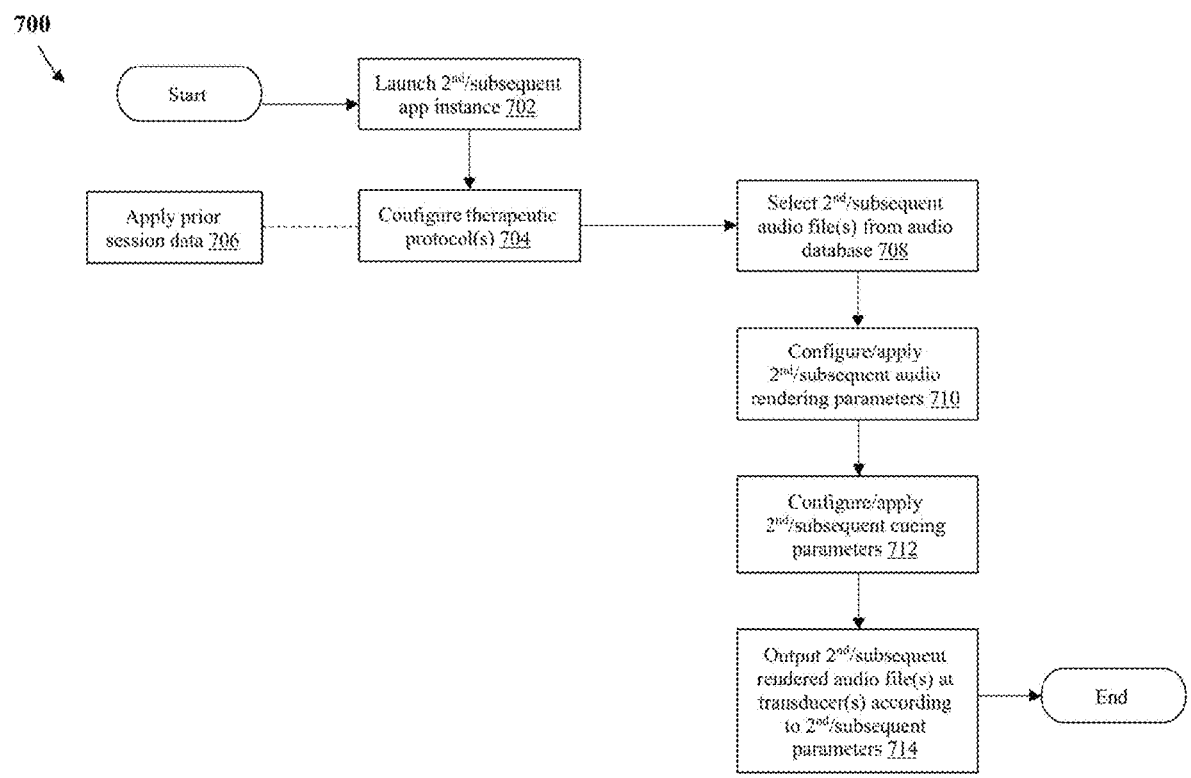
FIG. 7 is a functional block diagram of a routine of an audio processing system for environmental enrichment therapy, in accordance with certain aspects of the present disclosure.

Referring now to FIG. 7 (with certain references to FIG. 4), a functional block diagram of a routine 700 of an audio processing system for environmental enrichment therapy is shown. In accordance with certain aspects of the present disclosure, the audio processing system for environmental enrichment therapy may comprise system 300 of FIG. 3. In accordance with certain embodiments, routine 700 may comprise one or more processor-executable instructions executed on exemplary computing system environment 100 of FIG. 1 and/or exemplary computing system 200 of FIG. 2. In accordance with certain aspects of the present disclosure, routine 700 may be successive or sequential to one or more steps or operations of routines 400-600 of FIGS. 4-6 and/or may comprise one or more sub-steps or sub-routines of routines 400-600 of FIGS. 4-6.

In accordance with certain aspects of the present disclosure, routine 700 is sequential to routine 400, as shown in FIG. 4. Routine 700 may comprise one or more steps or operations for launching a second or subsequent instance of an environmental enrichment application at the end user device (Step 702). In certain embodiments, the instance of the environmental enrichment application may comprise end user instance 320' of environmental enrichment application 320, as shown in FIG. 3. Routine 700 may continue by performing one or more steps or operations for configuring one or more therapeutic protocols for the environmental enrichment application (Step 704). In certain embodiments, the one or more therapeutic protocols may comprise one or more protocols for configuring and delivering one or more environmental cues to an end user. In certain embodiments, Step 704 may comprise one or more steps or operations for applying a plurality of user data and/or user parameters from a plurality of prior sessions 706 for personalizing the one or more environmental cues for the end user during the second or subsequent sessions of the environmental enrichment application. Routine 700 may proceed by performing one or more operations for selecting a second or subsequent audio file from the audio database (Step 708). In accordance with certain embodiments, the second or subsequent audio file may be different than the first audio file from routine 400. In accordance with certain embodiments, the second or subsequent audio files are selected in Step 708 in accordance with the configured therapeutic protocols from Step 704. Routine 700 may continue by performing one or more steps or operations for configuring and applying one or more second or subsequent audio rendering parameters to the second or subsequent audio files (Step 710). In accordance with certain embodiments, the second or subsequent rendering parameters are configured to manipulate one or more acoustic properties of the one or more audio files; for example, speed, pitch, volume, pan, filter cutoff, wavetable index, effects controls, frequency, rhythmicity, wavelength and the like. Routine 700 may proceed by executing one or more steps or operations for configuring and applying one or more second or subsequent cueing parameters and/or prompts to the second or subsequent audio files (Step 712). For example, the second or subsequent cueing parameters and/or prompts may comprise parameters for timing/trigger for delivery of a second or subsequent cue, duration of a second or subsequent cue, termination of a second or subsequent cue, and the like. Routine 700 may conclude by performing one or more steps or operations for outputting a second or subsequent rendered audio file comprising the final assembled output of Steps 708-712 at one or more transducers (Step 714). In accordance with certain embodiments, the one or more transducers may comprise the one or more speakers operably engaged with the end user device.

Figure 8:
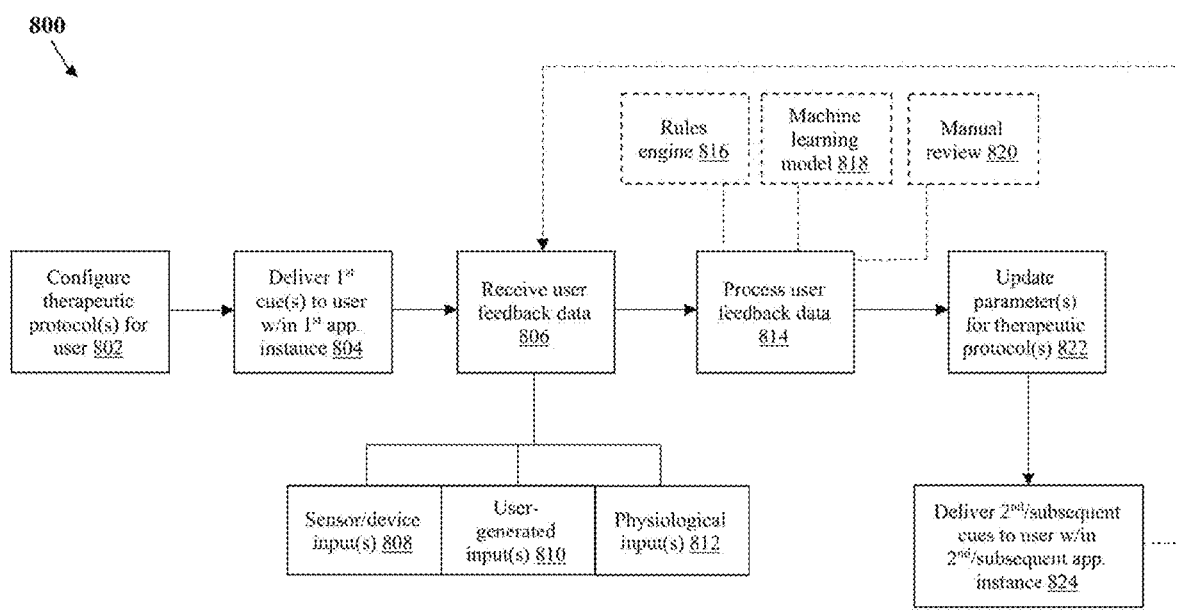
FIG. 8 is a functional block diagram of a routine of an audio processing system for environmental enrichment therapy, in accordance with certain aspects of the present disclosure.

Referring now to FIG. 8, a functional block diagram of a routine 800 of an audio processing system for environmental enrichment therapy is shown. In accordance with certain aspects of the present disclosure, the audio processing system for environmental enrichment therapy may comprise system 300 of FIG. 3. In accordance with certain embodiments, routine 800 may comprise one or more processor-executable instructions executed on exemplary computing system environment 100 of FIG. 1 and/or exemplary computing system 200 of FIG. 2. In accordance with certain aspects of the present disclosure, routine 800 may be successive or sequential to one or more steps or operations of routines 400-700 of FIGS. 4-7 and/or may comprise one or more sub-steps or sub-routines of routines 400-700 of FIGS. 4-7. In accordance with certain aspects of the present disclosure, routine 800 may comprise one or more steps or operations for personalizing one or more therapeutic cues for an end user across two or more instances of an environmental enrichment application.

In accordance with certain aspects of the present disclosure, routine 800 may be initiated by executing one or more steps or operations for configuring at least one therapeutic protocol for an end user within an environmental enrichment application (Step 802). The at least one therapeutic protocol may comprise one or more audio processing algorithms for configuring one or more personalized audio cues for the end user within the environmental enrichment application. In accordance with certain aspects of the present disclosure, routine 800 may proceed by executing one or more steps or operations for delivering a first audio cue (or cues) to the end user within a first instance of the environmental enrichment application (Step 804). Routine 800 may proceed by receiving user feedback data in response to delivering the first audio cue (or cues) to the end user within the first instance of the environmental enrichment application (Step 806). In accordance with certain embodiments, the user feedback data may be collected via one or more modalities. In certain embodiments, the user feedback data may be collected by the end user or alternatively may be collected by an administrative user or other stakeholder (e.g., a healthcare practitioner). In accordance with certain embodiments, one or more modalities may comprise one or more sensor inputs or end user device inputs 808 (e.g., accelerometer input from a smartphone or touchscreen input from a smartphone), one or more manual user-generated inputs 810 (e.g., a response to a questionnaire via a webform), and/or one or more physiological inputs 812 (e.g., a functional magnetic resonance imaging (fMRI) scan of the end user's brain to detect one or more changes in blood flow to the end user's brain before and after one or more sessions of the environmental enrichment application).

In accordance with certain aspects of the present disclosure, routine 800 may proceed by executing one or more steps or operations for processing the user feedback data (Step 814). In certain embodiments, step 814 may comprise processing the user feedback data according to one or more rules engine 816 and/or machine learning model 818. In accordance with certain embodiments, a rules engine 816 may comprise a pre-defined logic for modifying one or more parameters of the therapeutic protocol based on the user feedback data. In certain embodiments, a machine learning model 818 may comprise one or more supervised or unsupervised learning model configured to derive one or more cue-response patterns from the user feedback data. Machine learning model 818 may be configured to modify one or more parameters of the therapeutic protocol based on a model output to incrementally improve user outcomes for the environmental enrichment application. Exemplary frameworks for machine learning model 818 may include one or more classification or regression algorithms (e.g., Bayesian inference), reinforcement learning, artificial neural networks, deep learning, recurrent neural networks, convolutional neural networks, recurrent convolutional neural networks, cognitive computing and the like. In accordance with certain embodiments, step 814 may comprise one or more steps or operations for processing the user feedback data based on a manual review 820. Manual review 820 may comprise one or more steps or operations for presenting the user feedback data to an administrator user via a graphical user interface presented in administrator instance of the environmental enrichment application (e.g., admin user instance 320" of FIG. 3). The administrator instance of the environmental enrichment application may be configured to enable the administrator user to compare the user feedback data to a performance baseline for the end user and/or prior user feedback data or other performance metrics to enable the administrator user to determine a level of progress for the end user. Manual review 820 may comprise one or more steps or operations to enable the administrator user to configure and/or modify one or more parameters of the therapeutic protocol(s) via one or more administrator user inputs at the graphical user interface of the administrator instance of the environmental enrichment application. In accordance with certain aspects of the present disclosure, routine 800 may continue by performing one or more steps or operations for updating one or more parameters for the therapeutic protocol(s) based on an output of step 814 (Step 822). Routine 800 may proceed by delivering a second or subsequent cue to the user within a second or subsequent end user instance of the environmental enrichment application based on the output of step 822 (Step 824). In accordance with certain aspects of the present disclosure, step 824 may proceed to step 806 to enable a feedback loop for continuously modifying/updating the therapeutic protocol(s) across subsequent instances of the environmental enrichment application.

Figure 9:
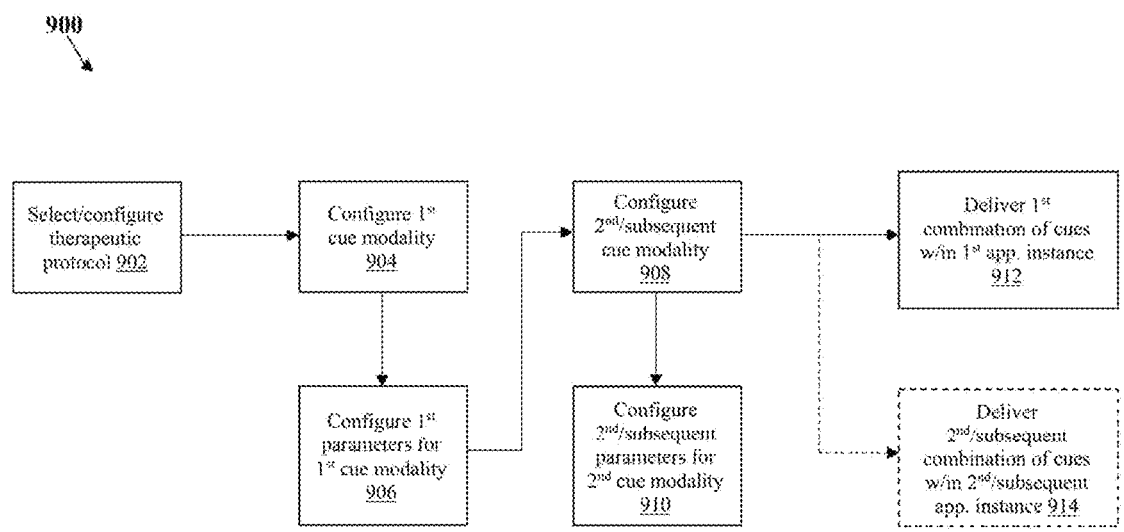
FIG. 9 is a functional block diagram of a routine of an audio processing system for environmental enrichment therapy, in accordance with certain aspects of the present disclosure.

Referring now to FIG. 9, a functional block diagram of a routine 900 of an audio processing system for environmental enrichment therapy is shown. In accordance with certain aspects of the present disclosure, the audio processing system for environmental enrichment therapy may comprise system 300 of FIG. 3. In accordance with certain embodiments, routine 900 may comprise one or more processor-executable instructions executed on exemplary computing system environment 100 of FIG. 1 and/or exemplary computing system 200 of FIG. 2. In accordance with certain aspects of the present disclosure, routine 900 may be successive or sequential to one or more steps or operations of routines 400-800 of FIGS. 4-8 and/or may comprise one or more sub-steps or sub-routines of routines 400-800 of FIGS. 4-8. In accordance with certain aspects of the present disclosure, routine 900 may comprise one or more steps or operations for configuring a combination of two or more cues comprising two or more cue modalities.

In accordance with certain aspects of the present disclosure, routine 900 commence by performing one or more operations for selecting and/or configuring at least one therapeutic protocol for delivering one or more cue to at least one end user within an environmental enrichment application (Step 902). In accordance with certain embodiments, routine 900 may proceed by configuring a first cue modality for a first cue (Step 904). The first cue modality may comprise an audio modality and the first cue may comprise an audio cue. Routine 900 may proceed by executing one or more steps or operations for configuring a first set of parameters for the first cue modality (Step 906). The first set of parameters for the first cue modality may comprise one or more parameters for selecting the first cue from a database of clinically validated cues or cue-types. The first set of parameters for the first cue modality may further comprise one or more parameters for configuring one of more audio characteristics of the first cue, wherein the first cue is an audio cue, including speed, pitch, volume, pan, filter cutoff, wavetable index, effects controls, frequency, rhythmicity, wavelength and the like. Routine 900 may proceed by executing one or more operations for configuring a second or subsequent cue modality for a second or subsequent cue (Step 908). The second or subsequent cue modality may comprise one or more of a wearable electronic device (e.g., smart watch or activity tracker device), smart glasses (e.g., such as augmented reality (AR) glasses or virtual reality (VR) goggles), one or more personal health monitoring device (e.g., a heart monitoring device, a fall-monitoring device, an activity tracker with one or more integrated physiological sensors, and/or a smart watch with one or more physiological sensors), headphones, loudspeakers/speakers or other audio transducers; smartphone or personal computing device with at least one output device, and/or other devices configured to output a cue to a user of the environmental enrichment application. In accordance with certain embodiments, the second or subsequent cue may comprise one or more cue type including, audio, visual, haptic, electronic, visual, behavioral and the like. Routine 900 may proceed by executing one or more steps or operations for configuring a second or subsequent set of parameters for the second or subsequent cue modality (Step 910). In accordance with certain embodiments, the second or subsequent set of parameters may comprise parameters for timing/trigger for delivery of a second or subsequent cue, duration of a second or subsequent cue, termination of a second or subsequent cue, and the like. Routine 900 may continue by executing one or more steps or operations for delivering a first combination of cues within a first instance of the environmental enrichment application to an end user (Step 912). In accordance with certain embodiments, the first combination of cues may comprise only the first cue modality, only the second or subsequent cue modality or a combination of both the first cue modality and the second or subsequent cue modality. For example, the first combination of cues may comprise only an audio cue, or alternatively, only a visual cue, or alternatively, a combination of a visual cue and an audio cue. In certain embodiments, the first combination of cues may comprise a combination of three or more cue modalities; for example, an audio cue, a visual cue and a haptic cue. In certain embodiments, routine 900 may comprise one or more steps or operations for delivering a second or subsequent combination of cues within a second or subsequent instance of the environmental enrichment application. In certain embodiments, the second or subsequent combination of cues is different from the first combination of cues. This may include a different combination of cue modalities or a different configuration of cue parameters or a combination thereof. In accordance with certain embodiments, the second or subsequent combination of cues may comprise only the first cue modality, only the second or subsequent cue modality or a combination of both the first cue modality and the second or subsequent cue modality. For example, the second or subsequent combination of cues may comprise only an audio cue, or alternatively, only a visual cue, or alternatively, a combination of a visual cue and an audio cue. In certain embodiments, the second or subsequent combination of cues may comprise a combination of three or more cue modalities; for example, an audio cue, a visual cue and a haptic cue.

Figure 10:
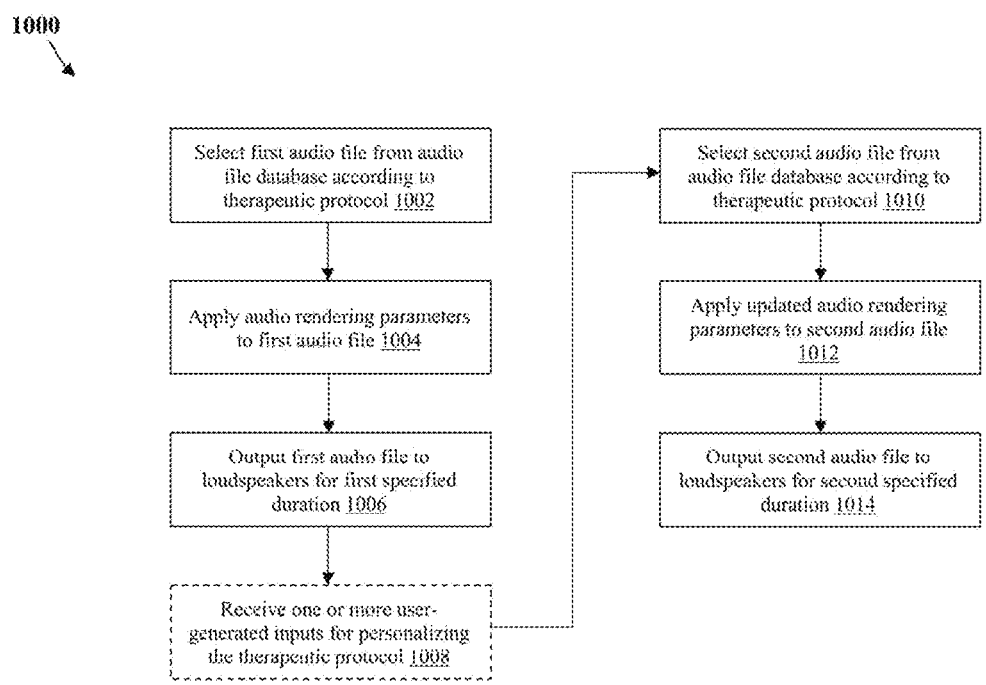
FIG. 10 is a process flow diagram of an audio processing method for environmental enrichment therapy, in accordance with certain aspects of the present disclosure.

Referring now to FIG. 10, a process flow diagram of an audio processing method 1000 for environmental enrichment therapy is shown. In accordance with certain aspects of the present disclosure, method 1000 may be implemented on exemplary computing system environment 100 of FIG. 1 and/or exemplary computing system 200 of FIG. 2. Method 1000 may be embodied with one or more routines 400-900 of FIGS. 4-9. In accordance with certain aspects of the present disclosure, method 1000 may commence by performing one or more steps or operations for selecting (e.g., with an audio processor) a first audio file from a plurality of audio files according to at least one therapeutic protocol (Step 1002). In accordance with certain embodiments, the first audio file comprises a recording of a clinically validated audio cue associated with the therapeutic protocol. In certain embodiments, the audio cue comprises a recorded or artificial sound from an environment; for example, a recorded or synthesized audio file of a person walking on a gravel path. Method 1000 may continue by executing one or more steps or operations for applying (e.g., with the audio processor) one or more audio rendering parameters to the first audio file (Step 1004). In certain embodiments, the audio rendering parameters may comprise parameters for manipulating one or more audio features of the first audio file. In certain embodiments, the one or more audio features may comprise one or more acoustic properties of the first audio file; for example, speed, pitch, volume, pan, filter cutoff, wavetable index, effects controls, frequency, rhythmicity, wavelength and the like. In accordance with certain aspects of the present disclosure, the therapeutic protocol may comprise one or more audio processing parameters for selecting the first audio file from the plurality of audio files and configuring the one or more audio rendering parameters. Method 1000 may continue by executing one or more steps or operations for outputting (e.g., with the audio processor operably engaged with a loudspeaker) an acoustic output of the first audio file to a listener for a specified duration (Step 1006). In accordance with certain aspects of the present disclosure, method 1000 may optionally continue by executing one or more steps or operations for receiving (e.g., with the audio processor) one or more user-generated inputs for selectively configuring the one or more audio processing parameters (Step 1008). In certain embodiments, the one or more user-generated inputs may comprise one or more inputs for personalizing the therapeutic protocol for the listener. In accordance with certain aspects of the present disclosure, the therapeutic protocol may comprise one or more parameters for selecting the first audio file from the plurality of audio files and configuring the one or more audio rendering parameters. In accordance with certain embodiments, the one or more audio rendering parameters are applied to the first audio file at two or more time-points during the specified duration. In certain embodiments, the one or more audio rendering parameters may be different between a first time-point and a second time-point in the two or more time-points during the specified duration. In certain embodiments, step 1006 may further comprise outputting the acoustic output at two or more separate instances, wherein each instance in the two or more separate instances comprises a separate time interval. In certain embodiments, one or both of the first audio file and the one or more audio rendering parameters are different between each instance in the two or more separate instances.

In accordance with certain aspects of the present disclosure, method 1000 may proceed by executing one or more steps or operations for further comprising selecting (e.g., with the audio processor) a second audio file from the plurality of audio files according to the therapeutic protocol (Step 1010). In certain embodiments, the second audio file may comprise a recording of a different audio cue from the first audio file. In certain embodiments, the second audio file may comprise a positive-reward cue or a negative-reward cue. Method 1000 may continue by executing one or more steps or operations for applying (e.g., with the audio processor) one or more updated or modified audio rendering parameters to the second audio file (Step 1012). In accordance with certain embodiments, the updated/modified audio rendering parameters may comprise parameters for manipulating one or more audio features of the second audio file. Method 1000 may continue by executing one or more steps or operations for outputting (e.g., with the audio processor operably engaged with the loudspeaker) an acoustic output of the second audio file sequentially or concomitantly with the acoustic output of the first audio file during the second specified duration (Step 1014). In certain embodiments, the updated/modified audio rendering parameters are applied to the second audio file at one or more time-points during the second specified duration.

Figure 11A:
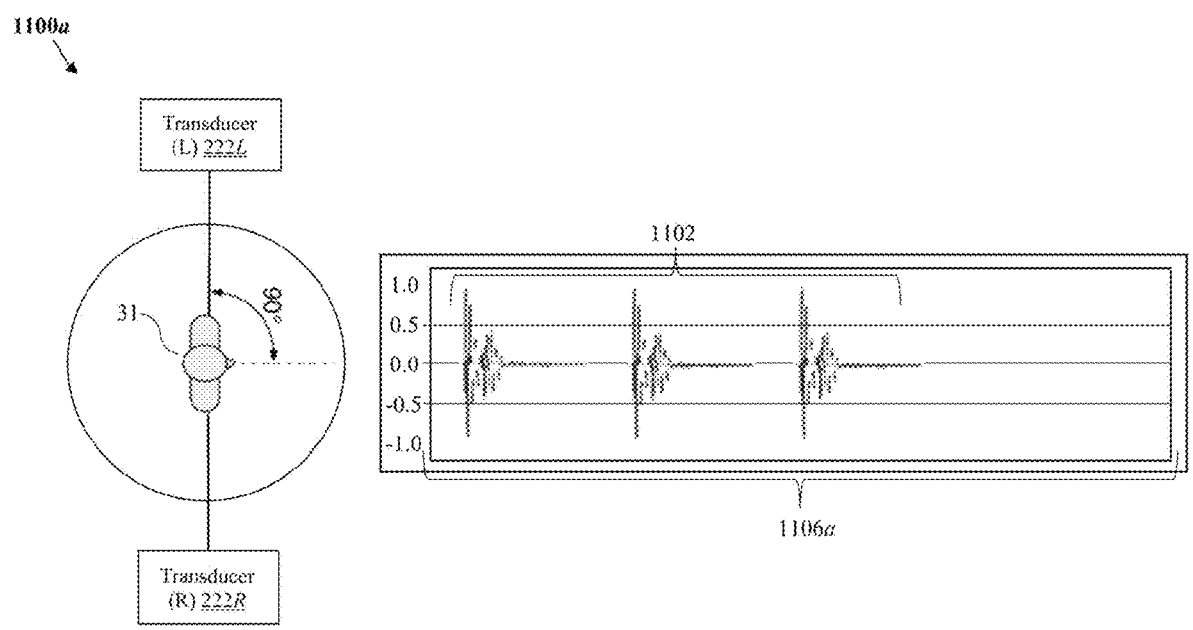
FIGS. 11A-11F are time/amplitude diagrams of an audio cue delivery within an audio processing method and system for environmental enrichment therapy, in accordance with certain aspects of the present disclosure.
Figure 11B:
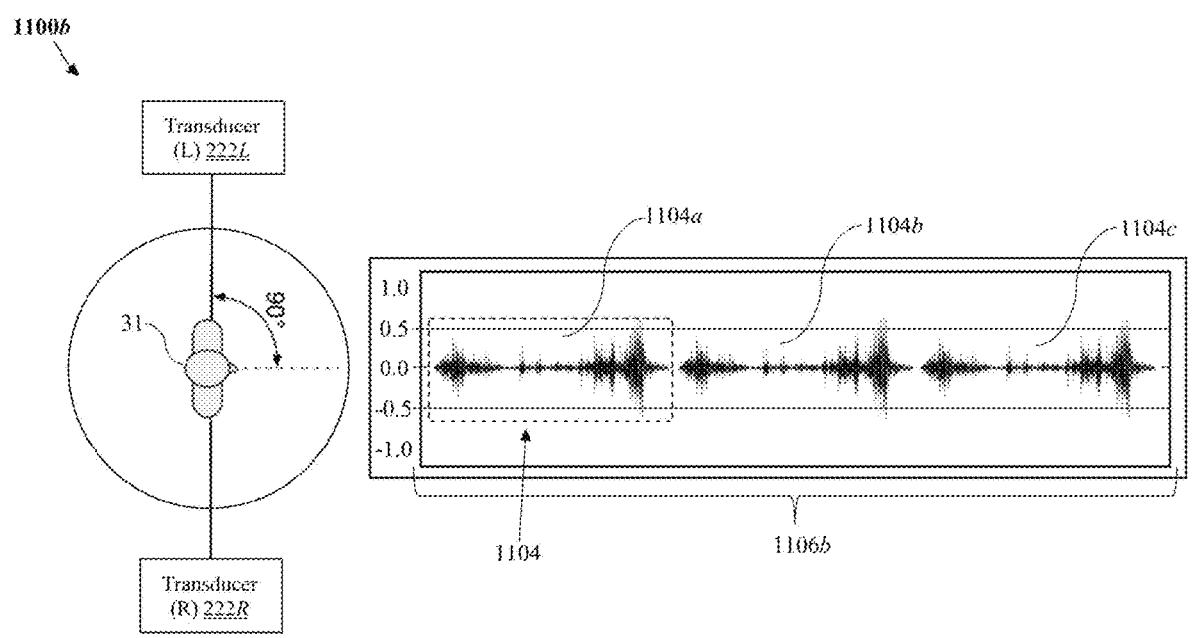
Figure 11C:
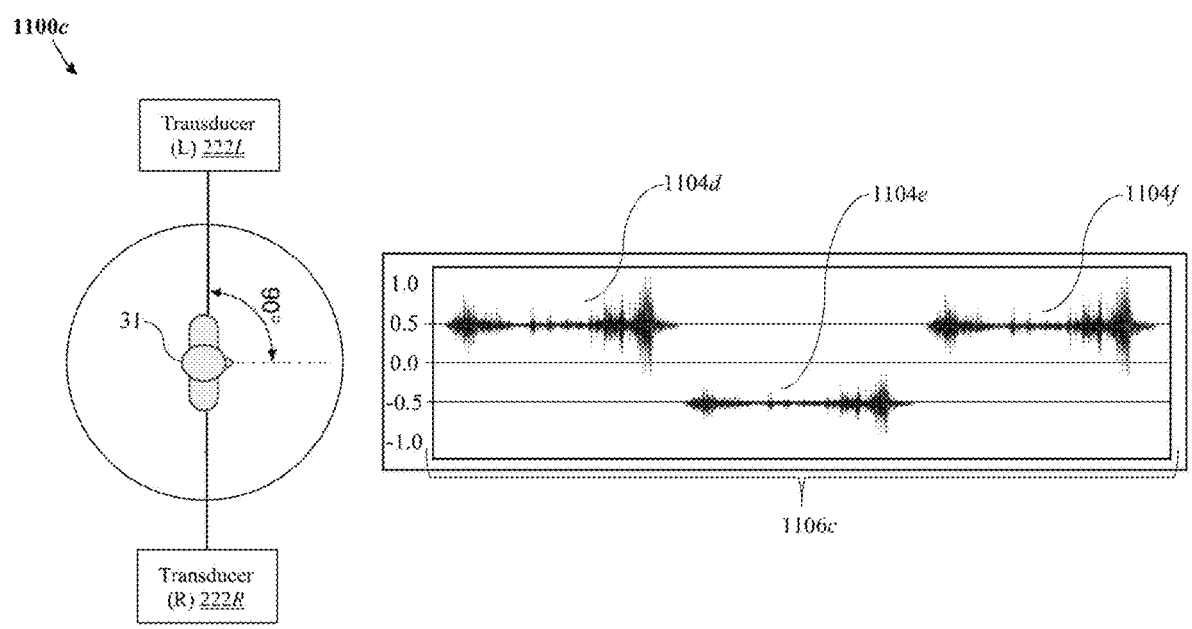

Referring now to FIGS. 11A-11F, time/amplitude diagrams for an audio processing method and system for environmental enrichment therapy are shown. In accordance with certain aspects of the present disclosure, the audio processing system may comprise system 300 of FIG. 3 and the audio processing method may comprise method 1000 of FIG. 10. As shown in FIGS. 11A-11F, end user 31 may be positioned in a sound field of left transducer 222L and right transducer 222R to receive an audio output from an environmental enrichment application. In certain embodiments, left transducer 222L and right transducer 222R may comprise a set of headphones or a pair of eyeglasses with integrated speakers. In accordance with certain aspects of the present disclosure, as shown in FIG. 11A, the environmental enrichment application may be configured to provide at least one initiation cue 1102 to end user 31 for a specified duration 1106*a*. In accordance with certain embodiments, initiation cue 1102 may comprise one or more anticipatory sound/auditory cues, a ramp up or ramp down in speed of an auditory cue, speech/voice cues or prompts (e.g., from health care provider or family member) and/or one or more artificial sounds (e.g., a synthesized sound that mimics the startup of a motor). In accordance with certain aspects of the present disclosure, as shown in FIG. 11B, the environmental enrichment application may be configured to output a series of a first audio cue 1104*a-c* for a specified duration 1106*b*. A first audio cue 1104 may comprise a clinically validated audio cue comprising a recorded or artificial sound from an environment; for example, a recording of a person walking on a gravel path. In accordance with certain aspects of the present disclosure, as shown in FIG. 11C, the environmental enrichment application may be configured to output, according to one or more audio processing parameters, a series of first audio cue 1104*d-f* for a specified duration 1106*c*. The one or more audio processing parameters may comprise parameters for modulating one or more acoustic characteristics of first audio cue 1104; for example, speed, pitch, volume, pan, filter cutoff, wavetable index, effects controls, frequency, rhythmicity, wavelength and the like. As shown in FIG. 11C, the one or more audio processing parameters are configured to modulate a pan of the acoustic output at transducers 222L and 222R such that audio cue 1104*d* is panned to 0.5, audio cue 1104*e* is panned to −0.5, and audio cue 1104*f* is panned to 0.5. As shown in FIG. 11C, the one or more audio processing parameters are configured to modulate a volume of the acoustic output at transducers 222L and 222R such that audio cue 1104*e* is output at a lower volume than audio cue 1104*d* and audio cue 1104*f*.

Figure 11D:
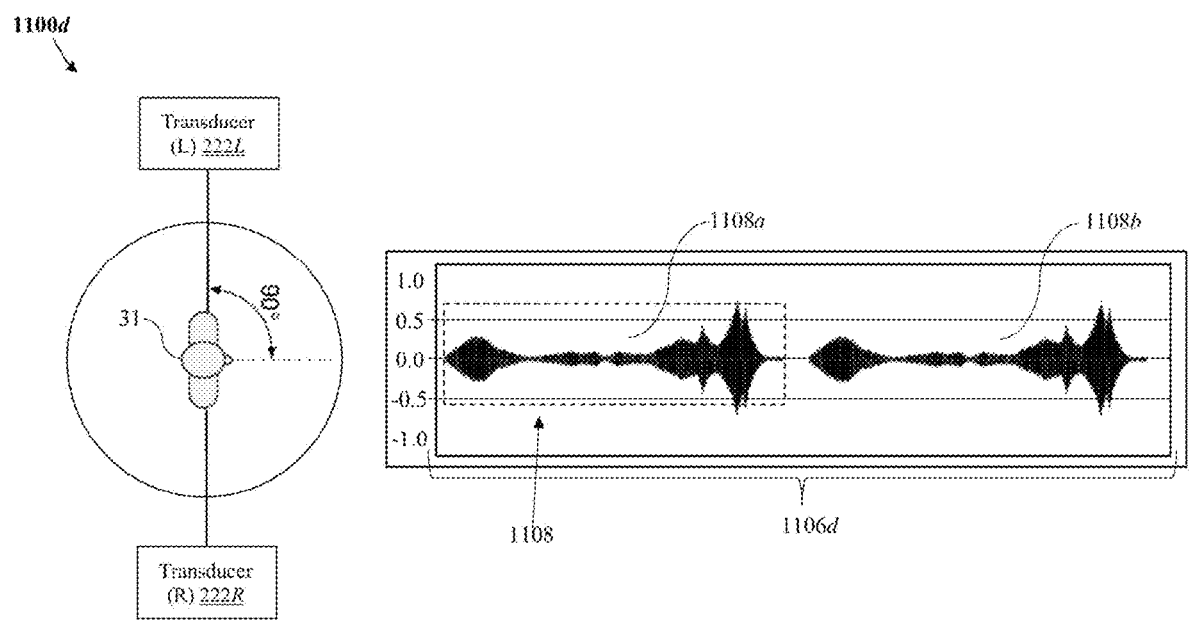
Figure 11E:
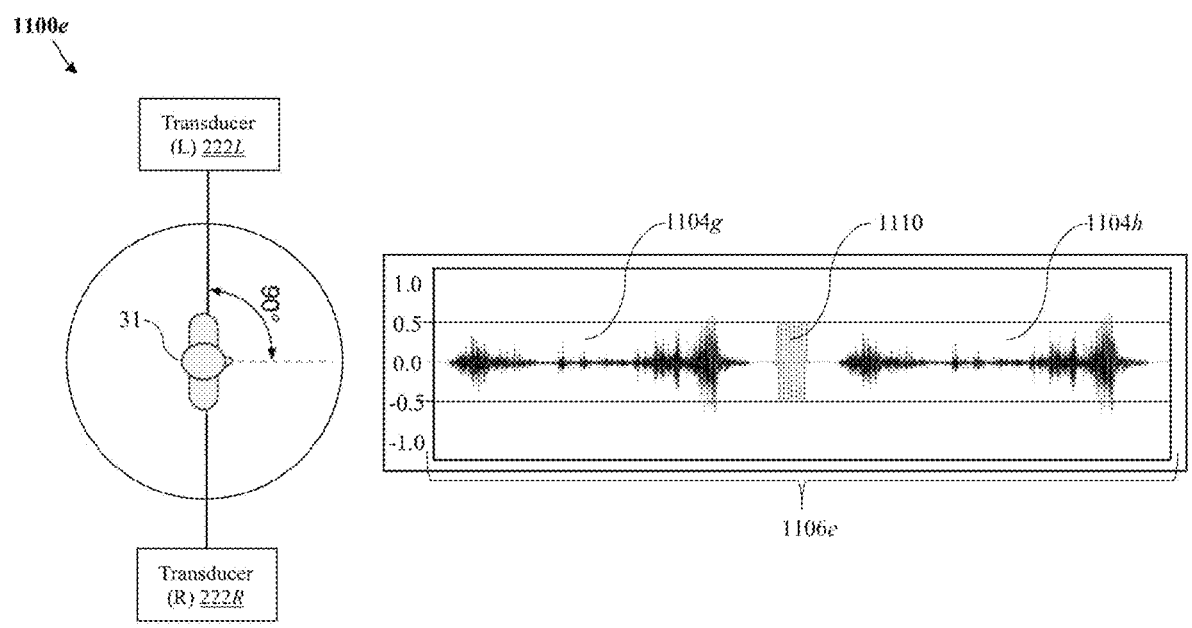
Figure 11F:
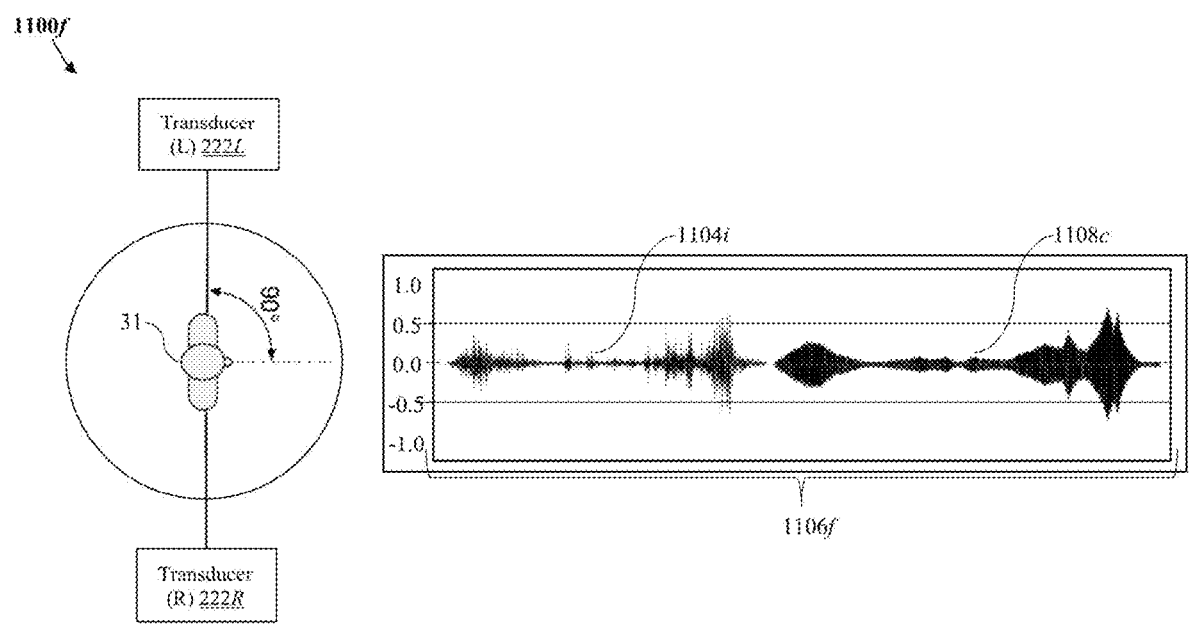

In accordance with certain aspects of the present disclosure, as shown in FIG. 11D, the environmental enrichment application may be configured to output, according to one or more audio processing parameters, a series of a second audio cue 1108*a-b* for a specified duration 1106*d*. In accordance with certain embodiments, second audio cue 1108 may comprise a different cue from first audio cue 1104. In certain embodiments, a clinically validated audio cue comprising a recorded or artificial sound from an environment; for example, a synthesized recording of a person walking in soled shoes in an interior corridor. In accordance with certain aspects of the present disclosure, as shown in FIG. 11E, the environmental enrichment application may be configured to output a reward cue 1110 at one or more timepoints in a specified duration 1106*e*. In certain embodiments, as shown in FIG. 11E, reward cue 1110 may be rendered during the same time duration as the clinically validated cues; e.g., 1104*g-h*. In certain embodiments, the reward file may comprise an audio prompt or notification configured to indicate to user 31 that a reward has been achieved/delivered within the environmental enrichment application. Reward cue 1110 may be configured to reinforce neuronal changes in the end user driven by the clinically validated cues; e.g., 1104*g-h*. Examples of positive reward cues may comprise a points-based system, visual rewards, monetary rewards, charitable contributions, "virtual points" to be used for rewards such as merchandise, experiential, gamification, and social interactions. In accordance with certain aspects of the present disclosure, as shown in FIG. 11F, the environmental enrichment application may be configured to output a combination of clinically validated cues; e.g., first audio cue 1104*i* and a second audio cue 1108*c*, during a specified duration 1106*f*. In accordance with certain aspects of the present disclosure, the environmental enrichment application may be configured to output a combination of clinically validated cues, as shown in FIG. 11F, in accordance with one or more audio processing parameters; e.g., audio processing parameters residing on at least one application server.

In accordance with certain aspects of the present disclosure, an audio processing method and system for environmental enrichment therapy may comprise one or more initiation cues presented to initiate an action of the listener and/or may comprise one or more action-relevant cues or prompts presented to a user at one or more time points during an environmental enrichment therapy session. For example, one or more initiation cues may include one or more breathing cues or prompts (e.g., presenting a recording of a person taking one or more deep breaths and/or a command for a user to take one or more deep breaths). Likewise, one or more action-relevant cues or prompts may be presented to the listener at one or more discrete time points or intervals during the environmental enrichment therapy session and/or throughout the entire duration of the environmental enrichment therapy session; for example, presenting a recording of a person taking one or more deep breaths and/or a command for a user to take one or more deep breaths at one or more time points during the environmental enrichment therapy session (e.g., continuously). In certain embodiments, the one or more action-relevant cues or prompts may comprise one or more cues or prompts to regularize the listener to a specific breathing pattern; e.g., a pattern, rhythm and/or timing of one or more in-breaths and/or out-breaths. In accordance with certain embodiments, the initiation cues or prompts and/or the action-relevant cues or prompts may include, but are not limited to, one or more recordings or prompts associated with breath or breathing, standing, sitting, walking, reaching, grabbing an object, placing an object, talking, and combinations thereof and the like.

As will be appreciated by one of skill in the art, the present invention may be embodied as a method (including, for example, a computer-implemented process, a business process, and/or any other process), apparatus (including, for example, a system, machine, device, computer program product, and/or the like), or a combination of the foregoing. Accordingly, embodiments of the present invention may take the form of an entirely hardware embodiment, an entirely software embodiment (including firmware, resident software, micro-code, etc.), or an embodiment combining software and hardware aspects that may generally be referred to herein as a "system." Furthermore, embodiments of the present invention may take the form of a computer program product on a computer-readable medium having computer-executable program code embodied in the medium.

Any suitable transitory or non-transitory computer readable medium may be utilized. The computer readable medium may be, for example but not limited to, an electronic, magnetic, optical, electromagnetic, infrared, or semiconductor system, apparatus, or device. More specific examples of the computer readable medium include, but are not limited to, the following: an electrical connection having one or more wires; a tangible storage medium such as a portable computer diskette, a hard disk, a random-access memory (RAM), a read-only memory (ROM), an erasable programmable read-only memory (EPROM or Flash memory), a compact disc read-only memory (CD-ROM), or other optical or magnetic storage device.

In the context of this document, a computer readable medium may be any medium that can contain, store, communicate, or transport the program for use by or in connection with the instruction execution system, apparatus, or device. The computer usable program code may be transmitted using any appropriate medium, including but not limited to the Internet, wireline, optical fiber cable, radio frequency (RF) signals, or other mediums.

Computer-executable program code for carrying out operations of embodiments of the present invention may be written in an object oriented, scripted or unscripted programming language such as Java, Perl, Smalltalk, C++, or the like. However, the computer program code for carrying out operations of embodiments of the present invention may also be written in conventional procedural programming languages, such as the "C" programming language or similar programming languages.

Embodiments of the present invention are described above with reference to flowchart illustrations and/or block diagrams of methods, apparatus (systems), and computer program products. It will be understood that each block of the flowchart illustrations and/or block diagrams, and/or combinations of blocks in the flowchart illustrations and/or block diagrams, can be implemented by computer-executable program code portions. These computer-executable program code portions may be provided to a processor of a general-purpose computer, special purpose computer, or other programmable data processing apparatus to produce a particular machine, such that the code portions, which execute via the processor of the computer or other programmable data processing apparatus, create mechanisms for implementing the functions/acts specified in the flowchart and/or block diagram block or blocks.

These computer-executable program code portions may also be stored in a computer-readable memory that can direct a computer or other programmable data processing apparatus to function in a particular manner, such that the code portions stored in the computer readable memory produce an article of manufacture including instruction mechanisms which implement the function/act specified in the flowchart and/or block diagram block(s).

The computer-executable program code may also be loaded onto a computer or other programmable data processing apparatus to cause a series of operational phases to be performed on the computer or other programmable apparatus to produce a computer-implemented process such that the code portions which execute on the computer or other programmable apparatus provide phases for implementing the functions/acts specified in the flowchart and/or block diagram block(s). Alternatively, computer program implemented phases or acts may be combined with operator or human implemented phases or acts in order to carry out an embodiment of the invention.

As the phrase is used herein, a processor may be "configured to" perform a certain function in a variety of ways, including, for example, by having one or more general-purpose circuits perform the function by executing particular computer-executable program code embodied in computer-readable medium, and/or by having one or more application-specific circuits perform the function.

Embodiments of the present invention are described above with reference to flowcharts and/or block diagrams. It will be understood that phases of the processes described herein may be performed in orders different than those illustrated in the flowcharts. In other words, the processes represented by the blocks of a flowchart may, in some embodiments, be in performed in an order other that the order illustrated, may be combined or divided, or may be performed simultaneously. It will also be understood that the blocks of the block diagrams illustrated, in some embodiments, merely conceptual delineations between systems and one or more of the systems illustrated by a block in the block diagrams may be combined or share hardware and/or software with another one or more of the systems illustrated by a block in the block diagrams. Likewise, a device, system, apparatus, and/or the like may be made up of one or more devices, systems, apparatuses, and/or the like. For example, where a processor is illustrated or described herein, the processor may be made up of a plurality of microprocessors or other processing devices which may or may not be coupled to one another. Likewise, where a memory is illustrated or described herein, the memory may be made up of a plurality of memory devices which may or may not be coupled to one another.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

While certain exemplary embodiments have been described and shown in the accompanying drawings, it is to be understood that such embodiments are merely illustrative of, and not restrictive on, the broad invention, and that this invention is not limited to the specific constructions and arrangements shown and described, since various other changes, combinations, omissions, modifications and substitutions, in addition to those set forth in the above paragraphs, are possible. Those skilled in the art will appreciate that various adaptations and modifications of the just described embodiments can be configured without departing from the scope and spirit of the invention. Therefore, it is to be understood that, within the scope of the appended claims, the invention may be practiced other than as specifically described herein.

What is claimed is:

1. An audio-processing method for environmental enrichment therapy comprising:
    selecting, with a processor, a first audio file from a plurality of audio files according to a therapeutic protocol, wherein the first audio file comprises an audio cue comprising a recorded or artificial sound from an environment,
    wherein the audio cue comprises at least one action-relevant cue comprising a sound of a person performing a specified action,
    wherein the specified action is selected from the group consisting of breathing, standing, sitting, walking, reaching, grabbing an object, placing an object, and talking;
    applying, with the processor, one or more audio rendering parameters to the first audio file according to the therapeutic protocol, wherein the one or more audio rendering parameters comprise parameters for manipulating one or more audio features of the first audio file, wherein the one or more audio features comprise one or more acoustic properties,
    wherein the one or more audio rendering parameters comprise parameters for modulating a distribution of a sound signal of the first audio file in a stereo field;
    generating, with the processor, a rendered audio file according to the therapeutic protocol; and
    outputting, with the processor operably engaged with a loudspeaker, an acoustic output of the rendered audio file to a listener for a specified duration according to the therapeutic protocol,
    wherein the therapeutic protocol comprises parameters for selecting the first audio file from the plurality of audio files according to the at least one action-relevant cue and parameters for configuring the one or more audio rendering parameters according to the at least one action-relevant cue,
    wherein the at least one action-relevant cue is configured to prompt at least one action by the listener, wherein the at least one action is associated with the at least one action-relevant cue according to the therapeutic protocol.

2. The audio-processing method of claim 1 further comprising selecting, with the processor, a second audio file from the plurality of audio files, wherein the second audio file comprises a recording of a different audio cue from the first audio file.

3. The audio-processing method of claim 2 further comprising outputting, with the processor operably engaged with the loudspeaker, an acoustic output of the second audio file sequentially or concomitantly with the acoustic output of the rendered audio file during the specified duration.

4. The audio-processing method of claim 3 wherein the second audio file comprises a positive-reward cue or a negative-reward cue.

5. The audio-processing method of claim 2 wherein the one or more audio rendering parameters comprise parameters for manipulating one or more audio features of the second audio file, wherein the one or more audio rendering parameters are applied to the second audio file at one or more time-points during the specified duration.

6. The audio-processing method of claim 1 further comprising receiving, with the processor, one or more user-generated inputs for selectively configuring the one or more audio rendering parameters, wherein the one or more user-generated inputs comprise one or more inputs for personalizing the therapeutic protocol for the listener.

7. The audio-processing method of claim 1 wherein the one or more audio rendering parameters are applied to the first audio file at two or more time-points during the specified duration, wherein the one or more audio rendering parameters are different between a first time-point and a second time-point in the two or more time-points during the specified duration.

8. The audio-processing method of claim 1 wherein outputting the acoustic output of the rendered audio file to the listener for the specified duration further comprises outputting the acoustic output at two or more separate instances, wherein each instance in the two or more separate instances comprises a separate time interval.

9. The audio-processing method of claim 8 wherein one or both of the first audio file and the one or more audio rendering parameters are different between each instance in the two or more separate instances.

10. An audio-processing system for environmental enrichment therapy comprising:
    a loudspeaker;
    a digital-to-analog converter operably engaged with the loudspeaker;
    an audio processing device operably engaged with the digital-to-analog converter; and
    at least one non-transitory computer readable storage medium operably engaged with the audio processing device, the at least one non-transitory computer readable storage medium having processor-executable instructions stored thereon that, when executed, cause the audio processing device to perform one or more operations, the one or more operations comprising:
        selecting a first audio file from a plurality of audio files according to a therapeutic protocol, wherein the first audio file comprises an audio cue comprising a recorded or artificial sound from an environment,
        wherein the audio cue comprises at least one action-relevant cue comprising a sound of a person performing a specified action,
        wherein the specified action is selected from the group consisting of breathing, standing, sitting, walking, reaching, grabbing an object, placing an object, and talking;
        applying one or more audio rendering parameters to the first audio file according to the therapeutic protocol, wherein the one or more audio rendering parameters comprise parameters for manipulating one or more audio features of the first audio file, wherein the one or more audio features comprise one or more acoustic properties,
        wherein the one or more audio rendering parameters comprise parameters for modulating a distribution of a sound signal of the first audio file in a stereo field;
        generating a rendered audio file according to the therapeutic protocol; and
        outputting, to the digital-to-analog converter operably engaged with the loudspeaker, an acoustic output of the rendered audio file to a listener for a specified duration according to the therapeutic protocol, wherein the therapeutic protocol comprises parameters for selecting the first audio file from the plurality of audio files according to the at least one action-relevant cue and parameters for configuring the one or more audio rendering parameters according to the at least one action-relevant cue, wherein the at least one action-relevant cue is configured to prompt at least one action by the listener, wherein the at least one action is associated with the at least one action-relevant cue according to the therapeutic protocol.

11. The audio-processing system of claim 10 wherein the one or more operations further comprise selecting a second audio file from the plurality of audio files, wherein the second audio file comprises a recording of a different audio cue from the first audio file.

12. The audio-processing system of claim 11 wherein the one or more operations further comprise outputting, to the digital-to-analog converter operably engaged with the loudspeaker, an acoustic output of the second audio file sequentially or concomitantly with the acoustic output of the rendered audio file during the specified duration.

13. The audio-processing system of claim 12 wherein the second audio file comprises a positive-reward cue or a negative-reward cue.

14. The audio-processing system of claim 11 wherein the one or more audio rendering parameters comprise parameters for manipulating one or more audio features of the second audio file, wherein the one or more audio rendering parameters are applied to the second audio file at one or more time-points during the specified duration.

15. The audio-processing system of claim 10 wherein the one or more operations further comprise receiving one or more user-generated inputs for selectively configuring the one or more audio rendering parameters, wherein the one or more user-generated inputs comprise one or more inputs for personalizing the therapeutic protocol for the listener.

16. The audio-processing system of claim 10 wherein the one or more audio rendering parameters are applied to the first audio file at two or more time-points during the specified duration, wherein the one or more audio rendering parameters are different between a first time-point and a second time-point in the two or more time-points during the specified duration.

17. The audio-processing system of claim 10 wherein outputting the acoustic output of the rendered audio file for the specified duration further comprises outputting the acoustic output at two or more separate instances, wherein each instance in the two or more separate instances comprises a separate time interval.

18. The audio-processing system of claim 17 wherein one or both of the first audio file and the one or more audio rendering parameters are different between each instance in the two or more separate instances.

19. The audio-processing system of claim 17 wherein the one or more operations further comprise outputting an acoustic output of a second audio file sequentially or concomitantly with the acoustic output of the rendered audio file during a second instance in the two or more separate instances.

20. A non-transitory computer readable storage medium having processor-executable instructions stored thereon that, when executed, cause one or more processors to perform one or more operations comprising:

selecting a first audio file from a plurality of audio files according to a therapeutic protocol, wherein the first audio file comprises an audio cue comprising a recorded or artificial sound from an environment, wherein the audio cue comprises at least one action-relevant cue comprising a sound of a person performing a specified action, wherein the specified action is selected from the group consisting of breathing, standing, sitting, walking, reaching, grabbing an object, placing an object, and talking;

applying one or more audio rendering parameters to the first audio file according to the therapeutic protocol, wherein the one or more audio rendering parameters comprise parameters for manipulating one or more audio features of the first audio file, wherein the one or more audio features comprise one or more acoustic properties, wherein the one or more audio rendering parameters comprise parameters for modulating a distribution of a sound signal of the first audio file in a stereo field;

generating a rendered audio file according to the therapeutic protocol; and outputting, to a digital-to-analog converter operably engaged with the loudspeaker, an acoustic output of the rendered audio file to a listener for a specified duration according to the therapeutic protocol, wherein the therapeutic protocol comprises parameters for selecting the first audio file from the plurality of audio files according to the at least one action-relevant cue and parameters for configuring the one or more audio rendering parameters according to the at least one action-relevant cue, wherein the at least one action-relevant cue is configured to prompt at least one action by the listener, wherein the at least one action is associated with the at least one action-relevant cue according to the therapeutic protocol.

* * * * *